(12) United States Patent
Kurashima et al.

(10) Patent No.: US 8,993,799 B2
(45) Date of Patent: Mar. 31, 2015

(54) METHOD FOR PRODUCING A PURIFIED NAPHTHALENE DICARBOXYLIC ACID

(75) Inventors: Hideharu Kurashima, Kurashiki (JP); Masayoshi Hayashi, Kurashiki (JP); Akio Hashimoto, Kurashiki (JP); Ryuusuke Shigematsu, Kurashiki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 11 days.

(21) Appl. No.: 14/122,547

(22) PCT Filed: May 30, 2012

(86) PCT No.: PCT/JP2012/063994
§ 371 (c)(1),
(2), (4) Date: Mar. 13, 2014

(87) PCT Pub. No.: WO2012/165506
PCT Pub. Date: Dec. 6, 2012

(65) Prior Publication Data
US 2014/0200364 A1    Jul. 17, 2014

(30) Foreign Application Priority Data
May 30, 2011    (JP) .................................. 2011-120464

(51) Int. Cl.
C07C 51/42    (2006.01)
C07C 51/487    (2006.01)

(52) U.S. Cl.
CPC ................................... *C07C 51/487* (2013.01)
USPC ........................................................ 562/486

(58) Field of Classification Search
CPC ....................................................... C07C 37/84
USPC ....................................................... 562/486
See application file for complete search history.

(56) References Cited

U.S. PATENT DOCUMENTS

| | | | |
|---|---|---|---|
| 5,565,609 A | 10/1996 | Hirowatari et al. | |
| 5,859,294 A * | 1/1999 | Hashimoto et al. | 562/486 |
| 6,452,047 B1 * | 9/2002 | Shigematsu et al. | 562/486 |

FOREIGN PATENT DOCUMENTS

| | | |
|---|---|---|
| DE | 697 08 942 T2 | 4/2002 |
| DE | 600 02 782 T2 | 3/2004 |
| EP | 0 787 712 A1 | 8/1997 |
| EP | 1 055 660 A1 | 11/2000 |
| ID | 15874 A | 8/1997 |
| JP | S50-135062 A | 10/1975 |
| JP | S50-142542 A | 11/1975 |
| JP | H09-208517 A | 8/1997 |
| JP | H09-208518 A | 8/1997 |
| JP | H10-53557 A | 2/1998 |
| JP | 2001-39921 A | 2/2001 |
| JP | 2011-116792 A | 6/2011 |
| KR | 2003-0072790 A | 9/2003 |
| TW | 446698 B | 7/2001 |
| WO | 94/18152 A1 | 8/1994 |

OTHER PUBLICATIONS

International Search Report dated Aug. 21, 2012, issued in International Application PCT/JP2012/063994.

* cited by examiner

*Primary Examiner* — Kamal Saeed
*Assistant Examiner* — Janet L Coppins
(74) *Attorney, Agent, or Firm* — Fitch, Even, Tabin & Flannery, LLP

(57) ABSTRACT

A method for producing a purified naphthalenedicarboxylic acid includes steps of mixing a naphthalenedicarboxylic acid-containing material and an amine in a mixed liquid of water and an organic solvent to give a crystal of a naphthalenedicarboxylic acid amine salt; and obtaining a purified naphthalenedicarboxylic acid from the crystal of the naphthalenedicarboxylic acid amine salt, wherein (1) in the step of forming the naphthalenedicarboxylic acid amine salt by adding an amine to the slurry that contains water, an organic solvent and a naphthalenedicarboxylic acid, the amine addition rate is from 0.002 to 0.4 mol/min relative to one mol of the naphthalenedicarboxylic acid, or (2) an amine is added to the aqueous solution prepared by dissolving the naphthalenedicarboxylic acid amine salt in water, or to the liquid prepared through solid-liquid separation of the aqueous solution to insolubilize and precipitate the metal component, and the precipitated metal component is removed through solid-liquid separation.

15 Claims, No Drawings

METHOD FOR PRODUCING A PURIFIED NAPHTHALENE DICARBOXYLIC ACID

CROSS-REFERENCE TO RELATED APPLICATIONS

This Application is a U.S. National Stage Application filed under 35 U.S.C. §371 of International Application PCT/JP2012/063994, filed May 30, 2012, designating the United States, which claims priority from Japanese Patent Application 2011-120464, filed May 30, 2011, the complete disclosures of which are hereby incorporated herein by reference in their entirety for all purposes.

TECHNICAL FIELD

The present invention relates to a method for producing a purified naphthalenedicarboxylic acid.

BACKGROUND ART

Naphthalenedicarboxylic acids are commercially important items as intermediates for chemical products, and in particular, have a widespread demand as starting materials for polyesters and polyamides that are used for fibers, bottles and films. Above all, 2,6-naphthalenedicarboxylic acid is useful as a starting material for polyethylene naphthalate (PEN) and aromatic liquid-crystal polymers having excellent physical characteristics and mechanical properties, and the demand for the acid is increasing these days.

As a method for producing a naphthalenedicarboxylic acid, there is known a method of oxidizing a naphthalene compound having two substituents with a molecular oxygen at high temperature and under high pressure in the presence of a heavy metal such as Co and Mn and a bromine compound in an acetic acid solvent. However, the product to be obtained according to the production method contains not only the intended naphthalenedicarboxylic acid but also, as an impurity, at least one selected from monocarboxylic acids and aldehydes that are intermediate products in oxidation reaction, catalysts-derived bromine adducts, and colored components and oxidation catalysts-derived metal components such as Co and Mn. The product that contains not only naphthalenedicarboxylic acid but also impurity is referred to as a crude naphthalenedicarboxylic acid.

When the crude naphthalenedicarboxylic acid is used as a starting material for polymer, the physical characteristics and the mechanical characteristics, such as heat resistance, mechanical strength, and dimensional stability, of the resin to be obtained are poor, and therefore the crude material is unsuitable as a starting material for polymer. In addition, the crude naphthalenedicarboxylic acid is generally colored in yellow, orange or black, and is therefore unsuitable for applications that require transparency such as bottles and films. Consequently, it is desired to increase the purity of naphthalenedicarboxylic acid by removing impurities, or that is, it is desired to develop an industrially advantageous production method for poorly-colored, high-purity naphthalenedicarboxylic acid.

In general, for purification of organic compounds, operation of distillation, crystallization, adsorption and the like is employed either singly or as combined. However, the self-decomposition temperature of naphthalenedicarboxylic acid is lower than the boiling point and the melting point thereof, and therefore the acid could not be purified through distillation. In addition, the acid is hardly soluble in various solvents, and is therefore difficult to purify through crystallization.

As in the above, the method of purifying the crude naphthalenedicarboxylic acid through conventional distillation or crystallization is difficult, and therefore a method of purifying the crude acid is proposed, which comprises reacting the naphthalenedicarboxylic acid with an amine to form an amine salt to thereby increase the solubility of the salt in water, alcohol or the like, then purifying the salt through crystallization or through treatment with active carbon, and thereafter decomposing the amine salt for purification of the acid.

PTL 1 discloses a method comprising dissolving a crude naphthalenedicarboxylic acid in an aqueous solution of an aliphatic amine, crystallizing the amine salt by cooling or condensation, and thereafter thermally decomposing the salt.

PTL 2 discloses a method for obtaining purified 2,6-naphthalenedicarboxylic acid, which comprises dissolving a crude 2,6-naphthalenedicarboxylic acid in an aqueous solution of an amine, then hydrogenating it and thereafter removing the amine compound through evaporation to thereby precipitate 2,6-naphthalenedicarboxylic acid.

PTL 3 discloses a method comprising crystallizing a naphthalenedicarboxylic acid amine salt with a water/ketone solvent and then decomposing the amine salt.

PTL 4 discloses a method comprising dissolving a salt of an aromatic dicarboxylic acid and an aliphatic amine and/or an alicyclic amine (hereinafter this may be referred to as an amine) in water, purifying it through adsorption to active carbon and thereafter heating it in the presence of water to decompose the amine salt.

PTL 5 discloses a method comprising blending a crude naphthalenedicarboxylic acid, an amine and a solvent containing water under the condition in which a crystal of a naphthalenedicarboxylic acid amine salt could precipitate out to give the crystal of the amine salt, and thereafter dissolving the amine salt crystal in water and then decomposing the salt.

PTL 6 discloses a method for producing a high-purity naphthalenedicarboxylic acid, which comprises dissolving a crude naphthalenedicarboxylic acid in an aqueous solution containing an aliphatic amine, then removing the heavy metal component through filtration or through filtration followed by solid adsorbent treatment in such a manner that the remaining heavy metal component could be at most 100 ppm relative to the naphthalenedicarboxylic acid, and thereafter heating the resulting aqueous solution to remove the amine through evaporation.

In PTL 6, a crude naphthalenedicarboxylic acid is dissolved in an aqueous amine solution and the metal component is precipitated out as an impurity, and thereafter the system is filtered through a filter having a pore size of at most 10 μm to separate the metal component. In addition, in this, there is given a description saying that in an industrial apparatus, it is better to gradually reduce the filter pore size in multistage filtration as preventing clogging and enabling long-term stable operation and that the heavy metal component hardly removable through filtration could be removed by additional solid adsorbent treatment.

CITATION LIST

Patent Literature

PTL 1: JP-A-50-135062
PTL 2: JP-A-50-142542
PTL 3: JP-A-10-053557
PTL 4: WO94/018152
PTL 5: JP-A-2001-039921
PTL 6: JP-A-9-208518

SUMMARY OF INVENTION

Technical Problem

However, according to the method described in PTL 1, the cost of the energy and the inert gas necessary for heating, cooling or condensation in crystallization is problematic. In addition, when the purified naphthalenedicarboxylic acid is desired to be collected at a high collection rate, then the impurities removal performance would lower and there may occur another problem in that the rate of purification of the naphthalenedicarboxylic acid would lower.

The present inventors investigated in detail the method described in PTL 2, resulting in the following. The hydrogenation described in Examples therein could remove formylnaphthoic that is an aldehyde impurity, however, methylnaphthoic acid formed during this precipitated out along with 2,6-naphthalenedicarboxylic acid in evaporation of the amine compound, and therefore could not be fully removed. Regarding the other impurities, bromine adducts, tricarboxylic acids and tetracarboxylic acids that are relatively hydrophilic impurities could be well removed, however, in addition to the above-mentioned methylnaphthoic acid, other impurities that are relatively poorly hydrophilic such as naphthoic acid, as well as trimellitic acid could be removed poorly.

According to the method described in PTL 3, a substantial energy cost is needed for crystallization, and therefore the method is insufficient in point of the process cost thereof.

The method described in PTL 4 mainly comprises decoloration and is defective as requiring a large amount of active carbon. In addition, the removal performance for organic impurities such as monocarboxylic acids and tricarboxylic acids is not high.

The method described in PTL 5 comprises merely blending a crude naphthalenedicarboxylic acid, an amine and a solvent containing water, in which the reaction from the crude naphthalenedicarboxylic acid crystal to a naphthalenedicarboxylic acid amine salt crystal, or that is, the reaction from the solid to the solid is carried out, not via a completely-dissolved state through heating operation therein. Consequently, the method has the advantage that the energy cost can be markedly reduced as compared with other conventional methods heretofore reported in the art, such as a method of dissolving an amine salt in water followed by cooling to give a purified crystal, a method of crystallization.

However, it has been found that, when the amine is added all at a time in forming the amine salt as in PTL 5, the formed amine salt crystal has a small particle size and therefore the method is insufficient for industrial production in the following points.

(1) Solid-liquid separation is difficult.
(2) In discharging and transferring the crystal cake, the system is clogged.
(3) The content of the mother liquid and the rinsing liquid in the amine salt crystal after solid-liquid separation is high, and therefore the recovery rate of the organic solvent from the mother liquid and the rinsing liquid is low.

In addition, PTL 5 says that the aromatic polycarboxylic acid amine salt from in the content of the organic impurities was reduced through salt forming operation is dissolved in water to give an aqueous solution thereof, and then foreign substances, insolubilized metal impurities and the like are removed from the solution through solid-liquid separation such as filtration, centrifugation and decantation.

Concretely, however, only filtration using a 1-μm filter is described therein as a laboratory process, but nothing is described therein relating to an industrial process. In addition, the present inventors investigated in detail the metal component separation method according to PTL 5, and have known that, when the naphthalenedicarboxylic acid amine salt from which the content of organic impurities had been reduced was merely dissolved in water, then a part of the metal component contained therein could not precipitate but was kept still dissolving in the solution, and the remaining part could not be separated and removed according to the method of filtration or the like. In other words, in the absence of treatment with a solid adsorbent or the like, the metal component could not be reduced to the desired level. Further, the inventors have additionally known that the insoluble metal component precipitated in dissolution of the naphthalenedicarboxylic acid amine salt in water has a small mean particle size of at most 10 μm and is viscous, and is therefore extremely difficult to separate.

According to the method of PTL 6, when the solid adsorbent treatment is not carried out, the content of the metal component could not be reduced to a level satisfactory as commercial product, and therefore the method is disadvantageous in point of labor supply. In addition, it is obvious that using the solid adsorbent is disadvantageous in point of cost and waste disposal.

The process flow comprises dissolution of a crude naphthalenedicarboxylic acid in an aqueous amine, metal component removal through filtration and by the use of a solid adsorbent, and decomposition of the naphthalenedicarboxylic acid amine salt. This process does not include a salt formation step that is an organic impurities removal step as in PTL 5. According to the process, the intended hue improvement and high recovery rate could be attained; however, when the hydrogenation is not carried out, the remaining amount of 2,6-formylnaphthoic acid (FNA) is 200 ppm in the best case, or that is, for reducing inorganic impurities, the process could not attain a sufficient purification level.

Even when the process flow comprises metal component separation, then salt formation and further naphthalenedicarboxylic acid amine salt decomposition, the salt from which the metal component has been removed is dissolved a large amount of water, and consequently, the salt formation step not requiring a large amount of water is extremely difficult and the process is inefficient.

Like PTL 5, PTL 6 has no description relating to an industrial filtration method. In addition, the present inventors carried out the laboratory method of multistage filtration (for example, the combination of filtration through the sintered metal filer having a pore size of 10 μm and filtration through the nitrocellulose membrane filter having a pore size of 1 μm, as in Example 3 in PTL 6), and judged that the metal filtration rate in the process is small and therefore the process is not an industrial one. Further, though the metal component in the products could be reduced through active carbon treatment, the process still requires the extremely complicated treatment.

The first object of the present invention is to provide a production method excellent in workability and process cost for producing a purified naphthalenedicarboxylic acid having a good hue from a crude naphthalenedicarboxylic acid.

The second object of the present invention is to provide a method for easily producing a naphthalenedicarboxylic acid having a good hue, containing few organic impurities and having a low metal content, from a crude naphthalenedicarboxylic acid at a low production cost, in a simplified manner and according to an industrial practice. More concretely, the present inventors have first found that in salt formation operation, a metal component is kept remaining in the formed naphthalenedicarboxylic acid amine salt, and by solving the problem, the inventors have succeeded in providing the production method for easily producing a naphthalenedicarboxylic acid having a low metal content, at a low production cost, in a simplified manner and according to an industrial practice.

Solution to Problem

The present inventors have made assiduous and detailed studies and have found that, in a process of adding an amine to a slurry containing water, an organic solvent and a naphthalenedicarboxylic acid to form a naphthalenedicarboxylic acid amine salt, when the amine addition rate is made to fall within a specific range, then the particle size of the crystal of the naphthalenedicarboxylic acid amine salt to be formed can be controlled and, as a result, a purified naphthalenedicarboxylic acid can be produced advantageously on an industrial scale, and have reached the present invention.

Specifically, the first aspect of the present invention is to provide a method for producing a purified naphthalenedicarboxylic acid as follows.

A method for producing a purified naphthalenedicarboxylic acid, comprising:

(A1) a step of mixing a naphthalenedicarboxylic acid-containing material and an amine in a mixed liquid of water and an organic solvent to give a crystal of a naphthalenedicarboxylic acid amine salt; and (A2) a step of obtaining a purified naphthalenedicarboxylic acid from the crystal of the naphthalenedicarboxylic acid amine salt obtained in the step (A1), wherein:

the step (A1) comprises:

(A11) a step of adding a naphthalenedicarboxylic acid-containing material to a mixed liquid of water and an organic solvent to prepare a slurry in which the naphthalenedicarboxylic acid has dispersed therein;

(A12) a step of adding an amine to the slurry prepared in the step (A11) to form a naphthalenedicarboxylic acid amine salt, thereby preparing a slurry in which a crystal of the naphthalenedicarboxylic acid amine salt has dispersed; and (A13) a step of processing the slurry prepared in the step (A12) for solid-liquid separation to separate the crystal of the naphthalenedicarboxylic acid amine salt, and the amine addition rate in the step (A12) is from 0.002 to 0.4 mol/min relative to one mol of the naphthalenedicarboxylic acid.

In addition, the present inventors further made assiduous studies and, as a result, have found that, when a crystal of a naphthalenedicarboxylic acid amine salt is obtained by mixing a naphthalenedicarboxylic acid-containing material and an amine in a mixed liquid of water and an organic solvent and then an aqueous solution of a naphthalenedicarboxylic acid amine salt is prepared by dissolving the crystal of the naphthalenedicarboxylic acid amine salt in water, a metal component contained in the aqueous solution of the naphthalenedicarboxylic acid amine salt can be removed either through treatment of adding an amine to the aqueous solution of the naphthalenedicarboxylic acid amine salt to insolubilize and precipitate the metal component contained in the aqueous solution followed by removing the precipitated metal component through solid-liquid separation; or through treatment of adding an amine to a liquid obtained by processing the aqueous solution of the naphthalenedicarboxylic acid amine salt through solid-liquid separation to thereby insolubilize and precipitate the metal component contained in the liquid obtained through the solid-liquid separation, followed by removing the precipitated metal component through solid-liquid separation, and have reached the present invention.

Specifically, the second aspect of the present invention is to provide a method for producing a purified naphthalenedicarboxylic acid as follows.

A method for producing a purified naphthalenedicarboxylic acid, comprising:

(B1) a step of mixing a naphthalenedicarboxylic acid-containing material and an amine in a mixed liquid of water and an organic solvent to give a crystal of a naphthalenedicarboxylic acid amine salt; and (B2) a step of obtaining a purified naphthalenedicarboxylic acid from the crystal of the naphthalenedicarboxylic acid amine salt obtained in the step (B1), wherein:

the step (B2) comprises:

(B21) a step of dissolving the crystal of the naphthalenedicarboxylic acid amine salt obtained in the step (B1) in water to prepare an aqueous solution of the naphthalenedicarboxylic acid amine salt;

(B22) a step of removing a metal component from the aqueous solution of the naphthalenedicarboxylic acid amine salt prepared in the step (B21); and (B23) a step of obtaining a purified naphthalenedicarboxylic acid from the aqueous solution of the naphthalenedicarboxylic acid amine salt from which the metal component has been removed in the step (B22), in the step (B22), the metal component is removed from the aqueous solution of the naphthalenedicarboxylic acid amine salt through:

(a) treatment of adding an amine to the aqueous solution of the naphthalenedicarboxylic acid amine salt prepared in the step (B21) to thereby insolubilize and precipitate the metal component contained in the aqueous solution, followed by removing the precipitated metal component though solid-liquid separation; or (b) treatment of adding an amine to a liquid obtained through solid-liquid separation of the aqueous solution of the naphthalenedicarboxylic acid amine salt prepared in the step (B21) to thereby insolubilize and precipitate the metal component contained in the liquid obtained through the solid-liquid separation, followed by removing the precipitated metal component though solid-liquid separation.

Advantageous Effects of the Invention

According to the method for producing a purified naphthalenedicarboxylic acid in the first aspect of the present invention, the crystal of the naphthalenedicarboxylic acid amine salt that is an intermediation in production of the purified naphthalenedicarboxylic acid can have a high purity and have a large particle size. Since the particle size of the amine salt crystal is large, (1) the solid-liquid separation is easy, (2) no clogging occurs during discharge and transfer of the crystal cake, and the crystal cake is easy to discharge and transfer, (3) the liquid content in the amine salt crystal (the amount of the mother liquid and the rinsing liquid in the amine salt crystal) is small, and the process cost can be reduced.

Accordingly, a purified naphthalenedicarboxylic acid can be produced advantageously on an industrial scale. The industrial meaning of the present invention is significant in purifying a naphthalenedicarboxylic acid.

According to the method for producing a purified naphthalenedicarboxylic acid in the second aspect of the present invention, an amine is added to the aqueous solution of the naphthalenedicarboxylic acid amine salt, or to a liquid obtained through solid-liquid separation of the aqueous solution of the naphthalenedicarboxylic acid amine salt to thereby promote the precipitation of the metal component, and accordingly, a high-purity naphthalenedicarboxylic acid can be produced with ease at a low production cost, in a simplified manner and according to an industrial practice. Since the method of the present invention is excellent in the industrial aspect thereof, the industrial meaning of the present invention is markedly significant.

DESCRIPTION OF EMBODIMENTS

<<First Aspect>>

The method for producing a purified naphthalenedicarboxylic acid according to the first aspect of the present invention comprises (A1) a step of mixing a naphthalenedicarboxylic acid-containing material and an amine in a mixed liquid of water and an organic solvent to give a crystal of a naphthalenedicarboxylic acid amine salt; and (A2) a step of obtaining a purified naphthalenedicarboxylic acid from the crystal of the naphthalenedicarboxylic acid amine salt obtained in the step (A1).

The step (A1) comprises (A11) a step of adding a naphthalenedicarboxylic acid-containing material to a mixed liquid of water and an organic solvent to prepare a slurry in which the naphthalenedicarboxylic acid has dispersed therein; (A12) a step of adding an amine to the slurry prepared in the step (A11) to form a naphthalenedicarboxylic acid amine salt, thereby preparing a slurry in which a crystal of the naphthalenedicarboxylic acid amine salt has dispersed; and (A13) a step of processing the slurry prepared in the step (A12) for solid-liquid separation to separate the crystal of the naphthalenedicarboxylic acid amine salt.

The amine addition rate in the step (A12) is from 0.002 to 0.4 mol/min relative to one mol of the naphthalenedicarboxylic acid.

The steps are described hereinunder.

<Step (A1): Step of Obtaining Naphthalenedicarboxylic Acid Amine Salt Crystal>

In the step (A1), a naphthalenedicarboxylic acid-containing material and an amine are mixed in a mixed liquid of water and an organic solvent to give a crystal of a naphthalenedicarboxylic acid amine salt.

The naphthalenedicarboxylic acid-containing material is a product obtained in a known process of producing a naphthalenedicarboxylic acid, and in general, the product contains not only the intended naphthalenedicarboxylic acid but also impurities. In the present invention, a purified naphthalenedicarboxylic acid having an increased purity is produced by removing the impurities. Hereinafter for differentiating the naphthalenedicarboxylic acid-containing material from the purified naphthalenedicarboxylic acid, the former may be referred to as "crude naphthalenedicarboxylic acid".

[Production of Crude Naphthalenedicarboxylic Acid]

As described above, the crude naphthalenedicarboxylic acid is one obtained in a known production method for producing a naphthalenedicarboxylic acid. The production method is not specifically defined. For example, the acid may be obtained through oxidation of a naphthalene having two substituents with a molecular oxygen in the presence of an oxidation catalyst. The substituents may be any ones capable of forming a carboxyl group through oxidation, and include, for example, an alkyl group such as a methyl group, an ethyl group, and an isopropyl group; and a formyl group, an acetyl group. As the oxidation catalyst, preferably used here is a catalyst containing a heavy metal such as Co and Mn, and bromine.

[Material for Oxidation]

With regard to the naphthalene having two substituents (hereinafter this may be referred to as "disubstituted naphthalene compound"), 2,6-substitutions, 2,7-substitutions and 1,5-substitutions are especially advantageous as the materials for polyesters, urethanes, liquid-crystal polymers, etc. Specific examples include dialkyl-substituted naphthalenes such as dimethylnaphthalene, diethylnaphthalene, diisopropylnaphthalane, and butyrylmethylnaphthalene; methylnaphthaldehyde and isopropylnaphthaldehyde. Above all, preferred are dialkyl-substituted naphthalenes.

[Oxidation Reaction Condition]

In the reaction of forming a crude naphthalenedicarboxylic acid, a disubstituted naphthalene compound is preferably oxidized with a molecular oxygen in the presence of an oxidation catalyst containing a heavy metal such as Co and Mn, and bromine.

It is preferable that the amount of the oxidation catalyst is from 0.05 to 2% by mass relative to the disubstituted naphthalene compound, the reaction temperature is from 120 to 250° C., and the oxygen partial pressure is a pressure not falling within the range of explosion (generally from 0.01 to 0.1 MPaG) in consideration of the total pressure.

The molecular oxygen-containing gas to be used as the oxidizing agent in the oxidation reaction includes air, oxygen diluted with an inert gas, oxygen-enriched air, etc. From the viewpoint of equipment and cost, in general, preferred is use of air.

[Crude Naphthalenedicarboxylic Acid]

The naphthalenedicarboxylic acid to be contained in the crude naphthalenedicarboxylic acid is preferably a 2,6-form, a 2,7-form or a 1,5-form. Each substitution may be suitably selected depending on the material to be oxidized and the oxidation reaction condition.

Of those isomers, more preferred is a 2,6-form (2,6-naphthalenedicarboxylic acid) as advantageous in industrial use.

The crude naphthalenedicarboxylic acid contains various organic impurities such as formylnaphthoic acid of an intermediate product in oxidation reaction, trimellitic acid formed in naphthalene ring decomposition, naphthalenedicarboxylic acid bromide with Br added thereto, and naphthalenetricarboxylic acid, in addition to colored components and oxidation catalyst metals.

<Step (A11): Step of Preparing Naphthalenedicarboxylic Acid-Dispersing Slurry>

In the step (A11), a naphthalenedicarboxylic acid-containing material is added to a mixed liquid of water and an organic solvent to prepare a slurry in which the naphthalenedicarboxylic acid has dispersed therein.

Regarding the blend ratio of water and the organic solvent in the mixed liquid, the amount of the organic solvent is preferably from 0.7 to 9 parts by mass, more preferably from 1 to 6 parts by mass, even more preferably from 1.5 to 4 parts by mass relative to 1 part by mass of water.

As the organic solvent, usable is a known organic solvent such as ketone, and acetonitrile. Preferred is ketone. More preferred are an aliphatic ketone and an alicyclic ketone; and even more preferred is an aliphatic ketone.

Specific examples of the aliphatic ketone include acetone, methyl ethyl ketone, methyl propyl ketone, diethyl ketone, methyl n-butyl ketone, methyl isobutyl ketone, 2-heptanone, 4-heptanone, diisobutyl ketone, acetonitrileacetone, etc. Specific examples of the alicyclic ketone include cyclohexanone and methylcyclohexanone. One or more of these organic solvents may be used here either singly or as combined.

Of those, especially preferred is acetone, which, when mixed with water, exhibits the property that the temperature dependence of the solubility thereof for a naphthalenedicarboxylic acid amine salt is the largest, and which is easy to handle and is readily available.

The content of the naphthalenedicarboxylic acid in the slurry is preferably from 5.0 to 50% by mass, more preferably from 10 to 40% by mass, even more preferably from 15 to 35% by mass.

<Step (A12): Step of Preparing Naphthalenedicarboxylic Acid Amine Salt-Dispersing Slurry>

In the step (A12), an amine is added to the slurry prepared in the step (A11) to form a naphthalenedicarboxylic acid amine salt, thereby preparing a slurry in which a crystal of the naphthalenedicarboxylic acid amine salt has dispersed.

Adding an amine to the slurry prepared in the step (A11) promotes the reaction of salt formation, and in the presence of a suitable amount of a solvent having a suitable water content, the salt formation reaction immediately occurs and goes on just after the start of the amine addition. The salt formation reaction does not go on in the absence of a solvent under the condition at room temperature and under normal pressure, and must be attained in a solvent. For the amine salt, water is a good solvent but ketone is a poor solvent, and therefore, when ketone alone is used as the solvent, the salt formation reaction also does not go on. In that manner, the reaction must be carried out in a solvent having a solubility for the amine salt.

The formed amine salt is dissolved in the mixed liquid up to saturation, and the amine salt fraction overstepping the limit amount of dissolution precipitates as a crystal, thereby giving a slurry in which the crystal of the amine salt has dispersed.

As the amine to be added in the step (A12), preferred are an aliphatic amine and an alicyclic amine. Specific examples of the aliphatic amine include methylamine, dimethylamine, trimethylamine, ethylamine, diethylamine, triethylamine, propylamine, dipropylamine; tripropylamine, isopropylamine, diisopropylamine, triisopropylamine, butylamine, dibutylamine, tributylamine, 2-ethylhexylamine, etc. Specific examples of the alicyclic amine include piperidine, N-methylpiperidine, pyrrolidine, ethyleneimine, hexamethyleneimine, etc. These amines may be used either singly or as a mixture thereof. Of those amines, preferred is a tertiary amine such as trimethylamine, triethylamine, tripropylamine, and triisopropylamine since the decomposition rate is high when the amine salt with a naphthalenedicarboxylic acid is decomposed and since the amine is easy to recover; and more preferred are triethylamine and trimethylamine.

The amount of the amine to be used is the equimolar amount or more relative to the carboxyl group of the naphthalenedicarboxylic acid in the slurry. The economical amount of the amine to be used in industrial practice is suitably from 1 to 1.5 equivalents relative to the carboxyl group.

In the first aspect of the present invention, the amine addition rate in the step (A12) is controlled to be from 0.002 to 0.4 mol/min relative to one mol of the naphthalenedicarboxylic acid in the slurry. At a lower amine addition rate, the quality of the salt crystal is better and the particle size thereof is larger. However, even though the rate is smaller than 0.002 molar times per minute, the effect could not be enhanced any more but the operation time would merely increase, and therefore such a low rate is industrially unfavorable. On the other hand, at a higher amine addition rate, the quality of the salt crystal becomes poorer and the particle size thereof is smaller. When the amine addition rate is higher than 0.4 molar times/min, then the crystal particle size to be obtained is too small therefore providing disadvantages in workability and process cost in that (1) the solid-liquid separation is difficult, (2) the line is clogged during discharge and transfer of crystal cake, and (3) the content of the mother liquid and the rinsing liquid in the amine salt crystal after solid-liquid separation is high and therefore the recovery rate of the organic solvent from the mother liquid and the rinsing liquid is low.

The amine addition rate is preferably from 0.005 to 0.4 mol/min, more preferably from 0.01 to 0.2 mol/min relative to one mol of the naphthalenedicarboxylic acid in the slurry.

The step (A12) is not via a completely-dissolved state of the system, differing from conventional crystallization, but is a reaction system from a solid (naphthalenedicarboxylic acid) to a solid (naphthalenedicarboxylic acid amine salt crystal). There has not been heretofore a report about a knowledge that, in such a reaction system, the limitation of the amine addition rate can enlarge the crystal particle size while maintaining the amine salt purification effect.

The slurry in which the thus-formed amine salt crystal has dispersed may be processed in the subsequent step (A13) to be mentioned below, directly as it is, but it is desirable that an organic solvent which is a poor solvent for the salt is added to the slurry and then the slurry is processed for the treatment of the step (A13). By adding the organic solvent thereto, the salt having been dissolved in the slurry could precipitate, and therefore the degree of crystallization to be defined according to the formula mentioned below can be increased. As the organic solvent to be added here, the same ones as the organic solvent in the step (A11) may be exemplified, and acetone is preferred.

Degree of Crystallization=(mass of amine salt crystal)/(total mass of amine salt)

<Step (A13): Step of Solid-Liquid Separation of Naphthalenedicarboxylic Acid Amine Salt-Dispersing Slurry>

In the step (A13), the slurry prepared in the step (A12) is processed for solid-liquid separation to give a crystal of the naphthalenedicarboxylic acid amine salt.

In the step (A13), the slurry prepared in the step (A12) is separated into the crystal and the mother liquid by a solid-liquid separator. In the mother liquid, impurities are dissolved at a high concentration, and therefore the crystal cake is rinsed for enhancing the quality of the crystal to be obtained. The amine added in an amount of more than the equivalent amount during salt formation is discharged out of the system in the rinsing step.

As the rinsing liquid, preferred are those not dissolving the amine salt crystal, and more preferred is acetone. As the solid-liquid separator, industrially used is a basket-type centrifuge, a rotary vacuum filter or the like. However, when the crystal particle size is small, then the load in the solid-liquid separator in the filtration step or in the rinsing step may increase and the cake flowability may worsen therefore bringing about a trouble of clogging during discharging and transferring the cake. Consequently, the crystal particle size is preferably larger.

In addition, when the crystal particle size is small, then the liquid content of the cake after solid-liquid separation or after rinsing may be high. In this case, the cake flowability may worsen, therefore bringing about the trouble of clogging during discharging and transferring the case and, in addition thereto, the loss of the rinsing liquid contained in the cake may increase uneconomically. Consequently, the crystal particle size is preferably larger.

The mean particle size of the crystal of the obtained naphthalenedicarboxylic acid amine salt is preferably 450 µm or more, more preferably 500 µm or more, even more preferably 600 µm or more. The mean particle size is measured according to a dry measurement method using a laser particle sizer.

The liquid content of the crystal of the obtained naphthalenedicarboxylic acid amine salt is preferably 3.5% by mass or less, more preferably 2.5% by mass or less, even more preferably 2.0% by mass or less.

The liquid content is calculated according to the following formula:

Liquid Content(% by mass)=$(a-b)/b \times 100$

[In the formula, a means the mass of the liquid-containing crystal cake, and is the mass of the crystal cake obtained after rinsing. b means the mass of the salt crystal cake in a dry state, as obtained by removing the liquid from the crystal cake.]

The crystal of the naphthalenedicarboxylic acid amine salt thus obtained may be processed in the step (A2) to be mentioned below, directly as it is; however, the crystal may be processed in the step (A2) after purified through recrystallization. The method of recrystallizing the crystal of the naphthalenedicarboxylic acid amine salt may be a method of dissolving the crystal by heating in the presence of a solvent followed by precipitating the crystal through operation of cooling, condensation or the like; or may be a method dissolving the amine salt in a solvent having a high solubility for the amine salt, such as water, and then adding thereto a solvent having a low solubility for the amine salt, such as acetone and alcohol, for precipitation of the crystal. The solvent to be used in the method is not always needed to be the same type as that of the solvent used in the step (A11), but from the industrial viewpoint, it is advantageous that the solvent is the same mixed liquid of water and an organic solvent as that used in the step (A11). Dissolving the naphthalenedicarboxylic acid amine salt in a solvent for crystallization markedly improves the hue of the salt, therefore making it possible to provide an extremely highly-purified naphthalenedicarboxylic acid amine salt having few organic impurities.

<Step (A2): Step of Producing Purified Naphthalenedicarboxylic Acid from Crystal of Naphthalenedicarboxylic Acid Amine Salt>

In the step (A2), a purified naphthalenedicarboxylic acid is separated from the crystal of the naphthalenedicarboxylic acid amine salt obtained in the step (A1).

It is preferable that the step (A2) comprises (A21) a step of dissolving the crystal of the naphthalenedicarboxylic acid amine salt obtained in the step (A1), in water to thereby prepare an aqueous solution of the naphthalenedicarboxylic acid amine salt; and (A22) a step of obtaining a purified naphthalenedicarboxylic acid from the aqueous solution of the naphthalenedicarboxylic acid amine salt prepared in the step (A21).

<Step (A21): Step of Preparing Aqueous Solution of Naphthalenedicarboxylic Acid Amine Salt>

In the step (A21), the crystal of the naphthalenedicarboxylic acid amine salt obtained in the step (A1) is dissolved in water to prepare an aqueous solution of the naphthalenedicarboxylic acid amine salt.

When the naphthalenedicarboxylic acid amine salt is dissolved in water, foreign substances, metal-containing impurities and others existing in the amine salt crystal may remain as solids therein without being dissolved. In such a case, it is preferable that the solids are removed through solid-liquid separation operation such as filtration, centrifugation, and decantation.

It is also preferable that an amine is added to the aqueous solution of the naphthalenedicarboxylic acid amine salt to precipitate the metal component in the aqueous solution and to remove the component. The metal component existing in the amine salt crystal may remain, as dissolved in water along with the amine salt therein, but when an amine is added to the aqueous solution, then the metal component could be insolubilized as a hydroxide thereof and may precipitate out. The precipitated metal hydroxide could be removed through filtration, centrifugation, decantation or the like. As the amine to be added here, the same ones as the amine in the step (A12) may be exemplified, and triethylamine and trimethylamine are preferred.

<Step (A22): Step of Obtaining Purified Naphthalenedicarboxylic Acid from Aqueous Solution of Naphthalenedicarboxylic Acid Amine Salt>

In the step (A22), a purified naphthalenedicarboxylic acid is obtained from the aqueous solution of the naphthalenedicarboxylic acid amine salt prepared in the step (A21).

In the step (A22), the concrete treatment method for obtaining a purified naphthalenedicarboxylic acid from the aqueous solution of the naphthalenedicarboxylic acid amine salt includes (1) a method of adding an acid having a higher degree of acidity than that of the naphthalenedicarboxylic acid to the aqueous solution in which the naphthalenedicarboxylic acid amine salt has been dissolved to thereby precipitate the naphthalenedicarboxylic acid, (2) a method of heating the aqueous solution of the naphthalenedicarboxylic acid amine salt directly as it is to thereby completely vaporize and remove water and the amine, (3) a method of heating the aqueous solution of the naphthalenedicarboxylic acid amine salt in the presence of water so as to decompose the amine salt and to remove water and the amine through evaporation, thereby precipitating the naphthalenedicarboxylic acid in the aqueous salt solution, etc.

In the method (1) of adding an acid having a higher degree of acidity than that of the naphthalenedicarboxylic acid to thereby precipitate the naphthalenedicarboxylic acid, an organic acid such as acetic acid and propionic acid, or an inorganic acid such as sulfuric acid and hydrochloric acid is added to the aqueous solution in which the naphthalenedicarboxylic acid amine salt has been dissolved to thereby precipitate the naphthalenedicarboxylic acid. In the method, fine crystals may readily precipitate out, and for solving the problem, therefore, the precipitation is attained at a high temperature of not lower than 100° C., preferably at 150° C., or the residence time is prolonged to thereby enlarge the particle size of the precipitated crystal. The precipitated crystal may be collected through solid-liquid separation according to a method of filtration, centrifugation or the like, and the obtained crystal may be washed with water or with the organic acid used in the process or the like, and further dried to give a purified naphthalenedicarboxylic acid.

In the method (2) of heating the aqueous solution of the naphthalenedicarboxylic acid amine salt directly as it is to thereby completely vaporize and remove water and the amine, the aqueous solution in which the naphthalenedicarboxylic acid amine salt has been dissolved is heated with stirring to decompose the amine salt, and the amine is completely evaporated away along with water to give a purified naphthalenedicarboxylic acid. Contrary to this, in the method (3) of heating the aqueous solution of the naphthalenedicarboxylic acid amine salt in the presence of water so as to decompose the amine salt and to remove water and the amine through evaporation, thereby precipitating the naphthalenedicarboxylic acid in the aqueous salt solution, the aqueous solution in which the naphthalenedicarboxylic acid amine salt has been dissolved is heated in the presence of water to decompose the amine salt, and water and the amine are evaporated away to thereby precipitate the naphthalenedicarboxylic acid in the aqueous salt solution. In this method, minor organic impurities that could not be removed in the step (A1) could still remain dissolved in the aqueous solution as amine salts therein, and therefore the purified naphthalenedicarboxylic acid can be obtained.

For salt decomposition in the presence of water, the decomposition method is not specifically defined. For example, the aqueous solution of the naphthalenedicarboxylic acid amine salt is put into a reactor for salt decomposition therein, then heated at a temperature not lower than the amine salt decomposition temperature to thereby decompose the salt, and the distillate that contains the released amine is collected. In this regard, the naphthalenedicarboxylic acid may precipitate in the reactor, and it is desirable that a given amount or more of water is kept existing in the reactor by supplying water thereinto during the treatment. When the amine salt decomposition rate has reached a predetermined level or more, preferably 50% or more, more preferably 90% or more, the salt decomposition is brought to a stop.

The amount of water to be used in salt decomposition may vary depending on the type of the naphthalenedicarboxylic acid and the amine, but preferably falls within a range of from 0.5 to 3 times by mass relative to the naphthalenedicarboxylic acid amine salt. When the heating temperature is too low, the amine salt decomposition rate would be uneconomically low, but when too high, then the amine and the naphthalenedicarboxylic acid would be degraded or colored. Therefore, the heating temperature preferably falls within a range of from 120 to 210° C. The pressure depends on the composition of the content at the temperature, but falls generally within a range of from −0.1 to 5 MPaG, preferably from 0 to 2 MPaG.

According to the above-mentioned methods, the naphthalenedicarboxylic acid amine salt is decomposed, and by cooling and collecting the generated amine, the total amount of the amine can be recovered. If desired, the amine may be purified and may be reused in the step (A1). At the same time of amine vaporization, a free naphthalenedicarboxylic acid is precipitated in the solution. The precipitated naphthalenedicarboxylic acid is collected through solid-liquid separation such as filtration and centrifugation. The acid may be optionally washed with water so that the impurities adhering to the crystal may be removed through the optional operation, etc.

The mother liquid and the crystal-washing liquid, after the solid-liquid separation, may be circulated in the step (A2), whereby the yield of the naphthalenedicarboxylic acid from the naphthalenedicarboxylic acid amine salt could be favorably increased. However, when the operation of circulating the total amount of the liquid is continued in the step (A2), impurities would excessively accumulate in the mother liquid at some stage and the quality of the crystal would worsen. Consequently, it is desirable that the mother liquid and the crystal-washing liquid are partially circulated in the step (A1) for recrystallization. The crystal may be dried to give a purified naphthalenedicarboxylic acid.

According to the method of decomposing the amine salt in the presence of water as in the above, organic impurities that could be relatively poorly removed in the step (A1), such as naphthalenetricarboxylic acids and Br-added naphthalenedicarboxylic acids, could be almost completely removed. In addition, the hue of the naphthalenedicarboxylic acid obtained here could be improved.

<<Second Aspect>>

The production method for a purified naphthalenedicarboxylic acid of the second aspect of the present invention comprises (B1) a step of mixing a naphthalenedicarboxylic acid-containing material and an amine in a mixed liquid of water and an organic solvent to give a crystal of a naphthalenedicarboxylic acid amine salt; and (B2) a step of obtaining a purified naphthalenedicarboxylic acid from the crystal of the naphthalenedicarboxylic acid amine salt obtained in the step (B1).

The step (B2) comprises (B21) a step of dissolving the crystal of the naphthalenedicarboxylic acid amine salt obtained in the step (B1) in water to prepare an aqueous solution of the naphthalenedicarboxylic acid amine salt; (B22) a step of removing a metal component from the aqueous solution of the naphthalenedicarboxylic acid amine salt prepared in the step (B21); and (B23) a step of obtaining a purified naphthalenedicarboxylic acid from the aqueous solution of the naphthalenedicarboxylic acid amine salt from which the metal component has been removed in the step (B22).

In the step (B22), the metal component is removed from the aqueous solution of the naphthalenedicarboxylic acid amine salt through (a) treatment of adding an amine to the aqueous solution of the naphthalenedicarboxylic acid amine salt prepared in the step (B21) to thereby insolubilize and precipitate the metal component contained in the aqueous solution, followed by removing the precipitated metal component though solid-liquid separation; or (b) treatment of adding an amine to a liquid obtained through solid-liquid separation of the aqueous solution of the naphthalenedicarboxylic acid amine salt prepared in the step (B21) to thereby insolubilize and precipitate the metal component contained in the liquid obtained through the solid-liquid separation, followed by removing the precipitated metal component though solid-liquid separation.

<Step (B1): Step of Obtaining Naphthalenedicarboxylic Acid Amine Salt Crystal>

In the step (B1), a naphthalenedicarboxylic acid-containing material and an amine are mixed in a mixed liquid of water and an organic solvent to give a crystal of a naphthalenedicarboxylic acid amine salt.

The naphthalenedicarboxylic acid-containing material in the step (B1) is the same as the naphthalenedicarboxylic acid-containing material in the step (A1) in the first aspect of the present invention, and its production method is also the same as in the latter.

The organic solvent for use in the mixed liquid in the step (B1) is the same as the organic solvent in the step (A11) in the first aspect of the present invention.

The blend ratio of water and the organic solvent in the step (B1) is the same as the blend ratio of water and the organic solvent in the step (A11) in the first aspect of the present invention.

The amine to be added in the step (B1) is the same as the amine in the step (A12) in the first aspect of the present invention.

It is preferable that the step (B1) comprises (B11) a step of adding a naphthalenedicarboxylic acid-containing material and an amine to a mixed liquid of water and an organic solvent to form a naphthalenedicarboxylic acid amine salt, thereby preparing a slurry in which a crystal of the naphthalenedicarboxylic acid amine salt has dispersed; and (B12) a step of processing the slurry prepared in the step (B11) for solid-liquid separation to separate the crystal of the naphthalenedicarboxylic acid amine salt.

<Step (B11): Step of Preparing Naphthalenedicarboxylic Acid Amine Salt-Dispersing Slurry>

In the step (B11), a naphthalenedicarboxylic acid-containing material and an amine are added to the mixed liquid of water and an organic solvent to form a naphthalenedicarboxylic acid amine salt, thereby preparing a slurry in which a crystal of the naphthalenedicarboxylic acid amine salt has dispersed.

In the step (B11) where a naphthalenedicarboxylic acid-containing material and an amine are added to the mixed liquid of water and an organic solvent, salt formation reaction occurs between the naphthalenedicarboxylic acid and the amine. The salt formation reaction does not go on in the absence of a solvent under the condition at room temperature and under normal pressure, and must be attained in a solvent. For the amine salt, water is a good solvent but ketone is a poor solvent, and therefore, when ketone alone is used as the solvent, the salt formation reaction also does not go on. In that manner, the reaction must be carried out in a solvent having a solubility for the amine salt.

The formed amine salt is dissolved in the mixed liquid up to saturation, and the amine salt fraction overstepping the limit amount of dissolution precipitates as a crystal, thereby giving a slurry in which the crystal of the amine salt has dispersed.

The amount of the amine to be used is the equivalent amount or more relative to the carboxyl group of the naphthalenedicarboxylic acid. The economical amount of the time in practical use is suitably from 1 to 1.5 equivalents relative to the carboxyl group.

The slurry in which the thus-formed amine salt crystal has dispersed may be processed in the subsequent step (B12) to be mentioned below, directly as it is, but it is desirable that an organic solvent which is a poor solvent for the salt is added to the slurry and then the slurry is processed for the treatment of the step (B12). By adding the organic solvent thereto, the salt having been dissolved in the slurry could precipitate, and therefore the degree of crystallization can be increased. As the organic solvent to be added here, the same ones as the organic solvent used in the above-mentioned mixed liquid may be exemplified, and acetone is preferred.

<Step (B12): Step of Solid-Liquid Separation of Naphthalenedicarboxylic Acid Amine Salt-Dispersing Slurry>

In the step (B12), the slurry prepared in the step (B11) is processed for solid-liquid separation to give a crystal of the naphthalenedicarboxylic acid amine salt.

In the step (B12), the slurry prepared in the step (B11) is separated into the crystal and the mother liquid by a solid-liquid separator. In the mother liquid, impurities are dissolved at a high concentration, and therefore the crystal cake is rinsed for enhancing the quality of the crystal to be obtained. As the rinsing liquid, preferred are those not dissolving the amine salt crystal, and more preferred is acetone. The amount added in salt formation in an amount of not lower than the equivalent amount is discharged out of the system in the rinsing step.

As the solid-liquid separator, industrially used is a basket-type centrifuge, a rotary vacuum filter or the like.

The crystal of the naphthalenedicarboxylic acid amine salt thus obtained may be processed in the step (B2) to be mentioned below, directly as it is; however, the crystal may be processed in the step (B2) after purified through recrystallization. The method of recrystallizing the crystal of the naphthalenedicarboxylic acid amine salt may be a method of dissolving the crystal by heating in the presence of a solvent followed by precipitating the crystal through operation of cooling, condensation or the like; or may be a method dissolving the amine salt in a solvent having a high solubility for the amine salt, such as water, and then adding thereto a solvent having a low solubility for the amine salt, such as acetone and alcohol, for precipitation of the crystal. The solvent to be used in the method is not always needed to be the same type as that of the solvent used in the step (B11), but from the industrial viewpoint, it is advantageous that the solvent is the same mixed liquid of water and an organic solvent as that used in the step (B11). Dissolving the naphthalenedicarboxylic acid amine salt in a solvent for crystallization markedly improves the hue of the salt, therefore making it possible to provide an extremely highly-purified naphthalenedicarboxylic acid amine salt having few organic impurities.

<Step (B2): Step of Producing Purified Naphthalenedicarboxylic Acid from Crystal of Naphthalenedicarboxylic Acid Amine Salt>

In the step (B2), a purified naphthalenedicarboxylic acid is separated from the crystal of the naphthalenedicarboxylic acid amine salt obtained in the step (B1).

The step (B2) comprises (B21) a step of dissolving the crystal of the naphthalenedicarboxylic acid amine salt obtained in the step (B1), in water to thereby prepare an aqueous solution of the naphthalenedicarboxylic acid amine salt; and (B22) a step of removing a metal component from the aqueous solution of the naphthalenedicarboxylic acid amine salt prepared in the step (B21); and (B23) a step of obtaining a purified naphthalenedicarboxylic acid from the aqueous solution of the naphthalenedicarboxylic acid amine salt from which the metal component has been removed in the step (B22).

<Step (B21): Step of Preparing Aqueous Solution of Naphthalenedicarboxylic Acid Amine Salt>

In the step (B21), the crystal of the naphthalenedicarboxylic acid amine salt obtained in the step (B1) is dissolved in water to prepare an aqueous solution of the naphthalenedicarboxylic acid amine salt.

In the step (B21), the crystal of the naphthalenedicarboxylic acid amine salt obtained in the step (B1) is dissolved in water, and in the step, at least a part of the metal component having mixed in the crystal could be also dissolved in water. Foreign substances, metal-containing impurities and others contained in the crystal may remain therein as solids without being dissolved in water.

<Step (B22): Step of Removing Metal Component from Aqueous Solution of Naphthalenedicarboxylic Acid Amine Salt>

In the step (B22), the metal component is removed from the aqueous solution of the naphthalenedicarboxylic acid amine salt prepared in the step (B21).

In the step (B22) of the second aspect of the present invention, the metal component is removed from the aqueous solution of the naphthalenedicarboxylic acid amine salt according to the following treatment (a) or (b).

(a) Treatment of adding an amine to the aqueous solution of the naphthalenedicarboxylic acid amine salt prepared in the step (B21) to thereby insolubilize and precipitate the metal component contained in the aqueous solution, followed by removing the precipitated metal component through solid-liquid separation.

(b) Treatment of adding an amine to a liquid obtained from solid-liquid separation of the aqueous solution of the naphthalenedicarboxylic acid amine salt prepared in the step (B21), to thereby insolubilize and precipitate the metal component contained in the liquid obtained from the solid-liquid separation, followed by removing the precipitated metal component through solid-liquid separation.

The treatment can sufficiently reduce the metal component to be in the finally-purified naphthalenedicarboxylic acid.

As described above, in the step (B21) where the crystal of the naphthalenedicarboxylic acid amine salt is dissolved therein, the metal component is also dissolved in water, and therefore in the step (B22), the metal component is insolubilized by adding an amine thereto, and is removed through solid-liquid separation.

In the treatment (b), in case where the foreign substances, metal-containing impurities and others contained in the crystal have remained in the aqueous solution as solids therein without being dissolved in water, the solids may be removed through solid-liquid separation before amine addition. However, even in the case where solids have remained in the aqueous solution in the step (B21), it is not always necessary to select the treatment (b), but the treatment (a) may also be selected in the case.

[Time of Insolubilization, and Sequence of Metal Component Separation Step]

The time of insolubilization, or that is, the time of amine addition is not specifically defined. It may be shown below along with the sequence of the metal component separation step that may be taken into consideration.

(I) Dissolution of naphthalenedicarboxylic acid amine salt in water→insolubilization→separation (II) Dissolution of naphthalenedicarboxylic acid amine salt in water→insolubilization→separation→separation (III) Dissolution of naphthalenedicarboxylic acid amine salt in water→separation→insolubilization→separation Of (I) to (III), any one is not always preferred, but may be selected depending on the separation method and the separator to be employed. Any of (I) to (III) enables metal separation with no problem.

[Solid-Liquid Separation Method and Separator to be Used]

Filtration and centrifugal sedimentation are preferred for the solid-liquid separation method in the treatment (a), and the two may be carried out each alone or as combined. A concrete solid-liquid separation method includes one-time filtration, two-time filtration, filtration followed by centrifugal sedimentation, one-time centrifugal sedimentation, two-time centrifugal sedimentation, and centrifugal sedimentation followed by filtration.

For the solid-liquid separation method before amine addition and the solid-liquid separation method after amine addition in the treatment (b), preferred are filtration and centrifugal sedimentation, like those for the solid-liquid separation method in the treatment (a); and the two may be carried out each alone or as combined. Preferably, the solid-liquid separation before amine addition is one-time filtration or one-time centrifugal sedimentation, and the solid-liquid separation after amine addition is one-time filtration or one-time centrifugal sedimentation.

The usable separator includes a horizontal filter leaf-type pressure strainer, an automatic filter paper-exchange pressure filter, an oscillating membrane separator and a ceramic membrane filter, all serving as a filter device; and a decanter-type centrifuge and a standard separation plate-type centrifugal settler both serving as a centrifugal settling device.

In case where the solid-liquid separation in the treatment (a) is one-time filtration, the filter apparatus is not specifically defined, and any and every apparatus can be used. However, preferred is use of a horizontal filter leaf-type pressure strainer, an automatic filter paper-exchange pressure filter and an oscillating membrane separator. In use of a horizontal filter leaf-type pressure strainer or an automatic filter paper-exchange pressure filter, preferably used is a filtration aid such as diatomaceous earth for precoating (forming a layer of the aid on the surface of filter) and body feeding (adding the aid to the liquid to be filtered). Precoating and body feeding could prevent filter clogging and could reduce filtration resistance.

In case where the solid-liquid separation in the treatment (a) is two-time filtration, and in case where the solid-liquid separation before amine addition is one-time filtration and the solid-liquid separation after amine addition is one-time filtration in the treatment (b), the filter apparatus to be used is not specifically defined, and any and every apparatus can be used and can be selected in consideration of the equipment held at present and the cost thereof. In this case, the performance of the filter apparatus to be used in the second stage may be lower than in the other case where filters alone are used, and the case may be more advantageous than in the other case where filters alone are used from the viewpoint of process cost. In case where a horizontal filter leaf-type pressure strainer or an automatic filter paper-exchange pressure filter is used, it is desirable that a filtration aid such as diatomaceous earth is used for precoating and body feeding.

In case where the solid-liquid separation in the treatment (a) is filtration followed by centrifugal sedimentation, and in case where the solid-liquid separation before amine addition is one-time filtration and the solid-liquid separation after amine addition is one-time centrifugal sedimentation in the treatment (b), the filter apparatus and the centrifugal sedimentation apparatus to be used are not specifically defined, and any and every type of apparatus can be used and can be selected in consideration of the equipment held at present and the cost thereof. When a horizontal filter leaf-type pressure strainer or an automatic filter paper-exchange pressure filter is used in the first-stage filtration, it is desirable that a filtration aid such as diatomaceous earth is used for precoating and body feeding.

In case where the solid-liquid separation in the treatment (a) is one-type centrifugal sedimentation, preferably, a standard separation plate-type centrifugal settler capable of providing a high-level centrifugal force is used as the separator.

In case where the solid-liquid separation in the treatment (a) is two-time centrifugal sedimentation, and in case where the solid-liquid separation before amine addition is one-time centrifugal sedimentation and the solid-liquid separation after amine addition is one-time centrifugal sedimentation in the treatment (b), the centrifugal sedimentation apparatus to be used is not specifically defined, but preferred is use of a decanter-type centrifugal separator for rough separation followed by a standard separation plate-type centrifugal settler. In this case, the performance of the standard separation plate-type centrifugal settler to be used in the second stage may be lower than that in the case where the standard separation plate-type centrifugal settler alone is used, and the case is therefore more advantageous than in the case where the standard separation plate-type centrifugal settler alone is used in point of the process cost.

In case where the solid-liquid separation in the treatment (a) is centrifugal sedimentation followed by separation, and in case where the solid-liquid separation before amine addition is one-time centrifugal sedimentation and the solid-liquid separation after amine addition is one-time filtration in the treatment (b), the centrifugal sedimentation apparatus and the filtration apparatus to be used are not specifically defined, and any and every type of apparatus can be used and can be selected in consideration of the equipment held at present and the cost thereof. When a horizontal filter leaf-type pressure strainer or an automatic filter paper-exchange pressure filter is used in the second-stage filtration, it is desirable that a filtration aid such as diatomaceous earth is used for precoating and body feeding.

[Atmosphere for Insolubilization and Metal Component Separation]

The atmosphere for the insolubilization (amine addition) and the metal component separation in the treatments (a) and (b) is not specifically defined, but preferred is an inert gas atmosphere. The inert gas includes argon, nitrogen, etc.; and preferred is nitrogen. As a result of the insolubilization in an inert gas atmosphere, the metal component such as cobalt and manganese dissolved in the aqueous solution of naphthalenedicarboxylic acid amine salt is insolubilized and precipitated as a hydroxide thereof.

[Amine and Amount Thereof for Use for Insolubilization]

As the amine to be added in the treatments (a) and (b), the same ones as the amine in the step (B1) may be exemplified, and triethylamine is preferred. The amine circulated and used in the step (B1) may be used for the insolubilization, or the amine circulated and used in the step (B22) may also be used in the step (B1).

In place of the amine, an inorganic base such as sodium hydroxide and potassium hydroxide may also be used for insolubilization and removal of the metal component such as cobalt and manganese dissolved in the aqueous salt solution; however, the inorganic base would cause a problem in that sodium or potassium derived from the inorganic base may remain in the aqueous salt solution.

The amount of the amine to be added may be determined in consideration of the amount of metal component such as cobalt and manganese dissolved in the aqueous solution of the naphthalenedicarboxylic acid amine salt prepared in the step (B21). In general, the amount is from 1 equivalent to 100 equivalents relative to the total amount of metal dissolved in the aqueous solution of the naphthalenedicarboxylic acid amine salt, preferably from 2 equivalents to 50 equivalents, more preferably from 5 equivalents to 20 equivalents. The equivalent means molar equivalent.

[Insolubilization Condition]

The temperature condition in insolubilization is not specifically defined, but is preferably from 25° C. to 80° C., more preferably from 40° C. to 70° C. In both the filtration and the centrifugal sedimentation for metal removal, the viscosity of the aqueous solution of the purified naphthalenedicarboxylic acid amine salt from which organic impurities have been removed is preferably lower, and therefore, the liquid temperature is preferably kept as such during the subsequent metal separation. The pressure condition is not also specifically defined. However, from the viewpoint of preventing amine vaporization, preferred is normal pressure or slightly-increased pressure. As long as the insolubilization time is 1 minute or longer, it is not specifically defined, but is preferably from 5 minutes to 60 minutes, more preferably from 10 minutes to 30 minutes.

<Step (B23): Step of Obtaining Purified Naphthalenedicarboxylic Acid from Aqueous Solution of Naphthalenedicarboxylic Acid Amine Salt>

In the step (B23), a purified naphthalenedicarboxylic acid is obtained from the aqueous solution of the naphthalenedicarboxylic acid amine salt from which the metal component has been removed in the step (B22).

The concrete treatment method for obtaining a purified naphthalenedicarboxylic acid from the aqueous solution of the naphthalenedicarboxylic acid amine salt in the step (B23) is the same as in the step (A22) in the first aspect of the present invention. Specifically, the treatment method includes (1) a method of adding an acid having a higher degree of acidity than that of the naphthalenedicarboxylic acid to the aqueous solution in which the naphthalenedicarboxylic acid amine salt has been dissolved to thereby precipitate the naphthalenedicarboxylic acid, (2) a method of heating the aqueous solution of the naphthalenedicarboxylic acid amine salt directly as it is to thereby completely vaporize and remove water and the amine, (3) a method of heating the aqueous solution of the naphthalenedicarboxylic acid amine salt in the presence of water so as to decompose the amine salt and to remove water and the amine through evaporation, thereby precipitating the naphthalenedicarboxylic acid in the aqueous salt solution, etc. Preferred is the method (3).

Examples

The method of the present invention is described in more detail with reference to Examples and Comparative Examples given below; however, the invention is not limited to these Examples.

The abbreviations shown in the following Examples, Comparative Examples and Tables are described below.

NDCA: 2,6-naphthalenedicarboxylic acid
NA: naphthoic acid
MNA: methylnaphthoic acid
FNA: formylnaphthoic acid
ANA: acetoxynaphthoic acid
TMA: trimellitic acid
Br-NDCA: naphthalenedicarboxylic acid bromide
NTCA: naphthalenetricarboxylic acid
TEA: triethylamine
NDCA-TEA: 2,6-naphthalenedicarboxylic acid triethylamine salt In the following Examples and Comparative Examples, the crude naphthalenedicarboxylic acid and the purified naphthalenedicarboxylic acid were evaluated according to the methods mentioned below.

Just as it was, the NDCA-TEA crystal could not be evaluated for the quality relating to the impurities therein, and for convenience' sake, therefore, the crystal was dried in vacuum at 110° C. for 3 hours to remove the amine to give a naphthalenedicarboxylic acid-containing crystal, and the resulting crystal was evaluated in the same manner.

[NDCA Purity and Organic Impurity Content]

After methyl esterification, the sample was analyzed through gas chromatography.

[Hue Value]

One g of the sample was dissolved in 10 ml of 1 N-sodium hydroxide aqueous solution, and using a quartz cell having a light path length of 10 mm, the absorbance thereof at 400 nm (hereinafter abbreviated as "OD400") was measured.

[Residual Metal Component]

After wet decomposition treatment, the sample was analyzed through ICP emission spectrometry.

[NDCA Recovery Rate]

The NDCA recovery rate is represented by the ratio of the amount of the naphthalenedicarboxylic acid contained in the naphthalenedicarboxylic acid-containing crystal to the amount of the naphthalenedicarboxylic acid in the crude naphthalenedicarboxylic acid fed in the system as the starting material.

[Particle Size of NDCA-TEA Crystal]

Using a laser particle sizer, the particle size of the crystal was measured according to a dry measurement method.

[Property of NDCA-TEA Cake]

The property of the NDCA-TEA cake was judged by the following criteria.

Bad: The cake was difficult to peel and transfer.
Problematic: The cake could be peeled and transferred, but the loss of the rinsing liquid (solvent) was great.
Good: The cake was in a well-peelable and transferable state, and the loss of the rinsing liquid was small.

Production Example A1

As an oxidation reactor, used here was a titanium-made autoclave having an internal volume of 3 L with an external heater, which was equipped with a stirrer, a reflux condenser, a starting material 2,6-dimethylnaphthalene supply duct, a solvent supply duct, an air supply duct and a reaction product discharge duct; and 2,6-naphthalenedicarboxylic acid was continuously produced therein.

The starting material 2,6-dimethylnaphthalene was heated at 130° C. for keeping it liquid, and using a piston-type pump, the material was supplied into the oxidation reactor. The solvent was previously prepared in a preparation tank by adding the catalyst component thereto, and also using a piston-type pump, the solvent was supplied into the oxidation reactor. The reaction liquid level was always controlled so as to be nearly 50% of the capacity of the reactor, and the reactor was driven under the controlled condition. The preparation tank was heated and controlled by an external heater. The supply amount of the starting material 2,6-dimethylnaphthalene and the supply amount of the solvent were as follows.
Supply amount of 2,6-dimethylnaphthalene: 300 g/hr
Supply amount of solvent, acetic acid: 1200 g/hr
Mass composition of other components of solvent:
Water: 5%
Mn: 2000 ppm
Co: 1000 ppm
Br: 3000 ppm Mn was added as manganese acetate 4-hydrate, Co was as cobalt acetate 4-hydrate, and Br was as hydrobromic acid. Compressed air was applied to the reactor at such a controlled supply rate that the oxygen concentration in the vent gas from the oxidation reactor could fall within a range of from 1.2 to 2.0%. The external heater was so controlled that the oxidation reaction temperature could be 210° C. as monitored by the thermometer inserted in the lower area of the middle stage in the reactor. The reaction pressure was controlled by the pressure control valve arranged downstream so that the pressure gauge arranged downstream of the reflux condenser could show 20 MPaG. The condensate liquid as condensed by the reflux condenser was partly discharged out of the system, and the remaining part thereof was refluxed into the oxidation reactor. The NDCA-containing slurry thus produced according to the above operation was filtered and dried to give a crude naphthalenedicarboxylic acid.

The crude naphthalenedicarboxylic acid had an NDCA purity of 97.00%, and contained 870 ppm or NA, 210 ppm of MNA, 7700 ppm of TMA, 3900 ppm of FNA, 330 ppm of ANA, 1600 ppm of Br-NDCA and 3200 ppm of NTCA as impurities.

Example A1

In a 500-mL glass-made three-neck flask equipped with a reflux condenser, a stirrer and a thermometric tube, 54.4 g of a starting material, crude naphthalenedicarboxylic acid obtained in Production Example A1 was added to a mixed liquid of 32.7 g of water and 54.9 g of acetone, and stirred therein. With stirring, 60.0 g of TEA was dropwise added thereto at a rate of 2.0 g/min for salt formation. From the NDCA purity of the crude naphthalenedicarboxylic acid, the amount of NDCA contained in the crude naphthalenedicarboxylic acid was calculated to be 52.8 g. Based on the NDCA amount, the amine addition rate was calculated, and the amine addition rate was 0.081 molar time/min relative to NDCA. Next, with stirring the slurry, 200 g of acetone was added thereto, and the salt having been dissolved in the mother liquid was crystallized. After the crystallization, the slurry temperature was controlled to be 25° C., and using a basket-type centrifuge, the slurry was processed for solid-liquid separation at a centrifugal force of 150 G, and then rinsed with 100 g of acetone. After the rinsing, the rotation of the basket-type centrifuge was kept for 30 seconds, and the residue was deliquored to remove the rinsing liquid. In this stage, the liquid content in the crystal was 1.8%. The cake property was good, and there occurred no problem in peelability from the filter cloth, the transferability and the flowability of the cake. The total cake was collected, and the rinsing liquid adhering thereto was removed by drying with air, thereby giving 101 g of a dry crystal of NDCA-TEA. The particle size and the liquid content of the NDCA-TEA crystal are shown in Table 1. The quality evaluation of the NDCA-TEA crystal is shown in Table 1. The NDCA recovery rate, as calculated from the amount of NDCA existing in the naphthalenedicarboxylic acid-containing crystal, was 95%.

101 g of the above NDCA-TEA crystal, 121 g of water and 12 g of TEA were mixed to prepare an aqueous NDCA-TEA solution. The aqueous NDCA-TEA solution was cloudy owing to the metal sludge therein. The solution was filtered through a 0.1 μm-filter to give a clear aqueous NDCA-TEA solution. The clear aqueous NDCA-TEA solution was put into a 500-mL SUS 304-made autoclave equipped with a condenser, a stirrer, a pressure filter and an aluminium block heater, and heated at 150° C., and with stirring at the temperature, ion-exchanged water was newly added thereto at a rate of 200 g/hr for salt decomposition with discharging the distillate in the same amount as that of the addition amount. The salt decomposition continued for 1 hour. Next, after left cooled down to 100° C., this was filtered under pressure, and the resulting crystal was washed with 100 g of water and dried at 110° C. for 3 hours. As a result, a sufficiently-purified, high-purity naphthalenedicarboxylic acid having the composition and the hue shown in Table 1 was obtained.

Example A2

NDCA-TEA was obtained in the same manner as in Example A1 except that TEA was dropwise added at a rate of 10.2 g/min (the amine addition rate was 0.41 molar time/min relative to NDCA). The liquid content of the cake was 3.2%, and the cake property was good. There was no problem in the peelability from the filter cloth, the transferability and the flowability of the cake. 101 g of a dry crystal of NDCA-TEA was obtained, and the NDCA recovery rate was calculated to be 95%. The particle size and the liquid content of the NDCA-TEA crystal are shown in Table 1. The quality evaluation of the NDCA-TEA crystal is shown in Table 1.

The NDCA-TEA crystal was processed for salt decomposition in the same manner as in Example A1. As a result, a sufficiently-purified, high-purity naphthalenedicarboxylic acid having the composition and the hue shown in Table 1 was obtained.

Example A3

NDCA-TEA was obtained in the same manner as in Example A1 except that TEA was dropwise added at a rate of 5.0 g/min (the amine addition rate was 0.20 molar time/min relative to NDCA). The liquid content of the cake was 2.2%, and the cake property was good. There was no problem in the peelability from the filter cloth, the transferability and the flowability of the cake. 101 g of a dry crystal of NDCA-TEA was obtained, and the NDCA recovery rate was calculated to be 95%. The particle size and the liquid content of the NDCA-TEA crystal are shown in Table 1. The quality evaluation of the NDCA-TEA crystal is shown in Table 1.

The NDCA-TEA crystal was processed for salt decomposition in the same manner as in Example A1. As a result, a sufficiently-purified, high-purity naphthalenedicarboxylic acid having the composition and the hue shown in Table 1 was obtained.

Example A4

NDCA-TEA was obtained in the same manner as in Example A1 except that TEA was dropwise added at a rate of 0.26 g/min (the amine addition rate was 0.011 molar time/min relative to NDCA). The liquid content of the cake was 1.7%, and the cake property was good. There was no problem in the peelability from the filter cloth, the transferability and the flowability of the cake. 101 g of a dry crystal of NDCA-TEA was obtained, and the NDCA recovery rate was calculated to be 95%. The particle size and the liquid content of the NDCA-TEA crystal are shown in Table 1. The quality evaluation of the NDCA-TEA crystal is shown in Table 1.

The NDCA-TEA crystal was processed for salt decomposition in the same manner as in Example A1. As a result, a sufficiently-purified, high-purity naphthalenedicarboxylic acid having the composition and the hue shown in Table 1 was obtained.

Example A5

NDCA-TEA was obtained in the same manner as in Example A1 except that TEA was dropwise added at a rate of 0.13 g/min (the amine addition rate was 0.0053 molar time/min relative to NDCA). The liquid content of the cake was 1.7%, and the cake property was good. There was no problem in the peelability from the filter cloth, the transferability and the flowability of the cake. 101 g of a dry crystal of NDCA-TEA was obtained, and the NDCA recovery rate was calculated to be 95%. The particle size and the liquid content of the NDCA-TEA crystal are shown in Table 1. The quality evaluation of the NDCA-TEA crystal is shown in Table 1.

The NDCA-TEA crystal was processed for salt decomposition in the same manner as in Example A1. As a result, a sufficiently-purified, high-purity naphthalenedicarboxylic acid having the composition and the hue shown in Table 1 was obtained.

Example A6

NDCA-TEA was obtained in the same manner as in Example A1 except that TEA was dropwise added at a rate of 0.051 g/min (the amine addition rate was 0.0021 molar time/min relative to NDCA). The liquid content of the cake was 1.6%, and the cake property was good. There was no problem in the peelability from the filter cloth, the transferability and the flowability of the cake. 101 g of a dry crystal of NDCA-TEA was obtained, and the NDCA recovery rate was calculated to be 95%. The particle size and the liquid content of the NDCA-TEA crystal are shown in Table 1. The quality evaluation of the NDCA-TEA crystal is shown in Table 1.

The NDCA-TEA crystal was processed for salt decomposition in the same manner as in Example A1. As a result, a sufficiently-purified, high-purity naphthalenedicarboxylic acid having the composition and the hue shown in Table 1 was obtained.

Comparative Example A1

NDCA-TEA was obtained in the same manner as in Example A1 except that 60.0 g of TEA was taken in a 100-ml beaker and added all at a time to the slurry. In this case, the amine addition time was about 10 seconds, and therefore, the addition rate was calculated to be about 15 molar time/min relative to NDCA. The liquid content of the cake was 10%. 101 g of a dry crystal of NDCA-TEA was obtained, and the NDCA recovery rate was calculated to be 95%. The particle size and the liquid content of the NDCA-TEA crystal are shown in Table 2. The quality evaluation of the NDCA-TEA crystal is shown in Table 2.

The particle size of the NDCA-TEA crystal was small, the liquid content thereof was high, and the property of the cake including peelability from filter cloth, transferability and flowability thereof was extremely bad. In industrial-scale application, there would be some risks of (a) difficulty in solid-liquid separation, (b) line clogging and (c) process cost increase. In addition, in the quality evaluation of the NDCA-TEA crystal, the OD400 value and the organic impurity content were extremely high as compared with those in Examples, or that is, the process could not attain a sufficient purification effect.

Comparative Example A2

An amine salt was obtained in the same manner as in Example A1 except that TEA was dropwise added at a rate of 12.0 g/min (the amine addition rate was 0.49 molar time/min relative to NDCA). The liquid content of the cake was 4.0%. 101 g of a dry crystal was obtained, and the NDCA recovery rate was calculated to be 95%. The particle size and the liquid content of the NDCA-TEA crystal are shown in Table 2. The quality evaluation of the NDCA-TEA crystal is shown in Table 2.

The particle size of the NDCA-TEA crystal was small, the liquid content thereof was high, and the peelability from filter cloth, the transferability and the flowability of the cake were worse than those in Examples. In industrial-scale application, there would be some risks of (a) difficulty in solid-liquid separation, (b) line clogging and (c) process cost increase. In addition, in the quality evaluation of the NDCA-TEA crystal, the organic impurity content was higher than in Examples, or that is, the process could not attain a sufficient purification effect.

Comparative Example A3

NDCA-TEA was obtained in the same manner as in Example A1 except that TEA was dropwise added at a rate of 20.0 g/min (the amine addition rate was 0.81 molar time/min relative to NDCA). The liquid content of the cake was 5.0%. 101 g of a dry crystal of NDCA-TEA was obtained, and the NDCA recovery rate was calculated to be 95%. The particle size and the liquid content of the NDCA-TEA crystal are shown in Table 2. The quality evaluation of the NDCA-TEA crystal is shown in Table 2.

The particle size of the NDCA-TEA crystal was small, and the liquid content thereof was high. In industrial-scale application, there would be some risks of (a) difficulty in solid-liquid separation, (b) line clogging and (c) process cost increase. In addition, in the quality evaluation of the NDCA-TEA crystal, the organic impurity content was higher than in Examples, or that is, the process could not attain a sufficient purification effect.

Comparative Example A4

NDCA-TEA was obtained in the same manner as in Example A1 except that TEA was dropwise added at a rate of 0.026 g/min (the amine addition rate was 0.0011 molar time/min relative to NDCA). The liquid content of the cake was 1.6%. 101 g of a dry crystal of NDCA-TEA was obtained, and the NDCA recovery rate was calculated to be 95%. The particle size and the liquid content of the NDCA-TEA crystal are shown in Table 2. The quality evaluation of the NDCA-TEA crystal is shown in Table 2. The quality of the liquid is on the same level as that in Example A6.

However, the time taken in adding TEA in the salt formation step was extremely large, and the process is not industrially practicable.

TABLE 1

|  |  | Example A1 | Example A2 | Example A3 | Example A4 | Example A5 | Example A6 |
|---|---|---|---|---|---|---|---|
| Amine Addition Rate (relative to NDCA, mol/min) | | 0.081 | 0.41 | 0.2 | 0.011 | 0.0053 | 0.0021 |
| Time taken by TEA addition (min) | | 30 | 5.9 | 12 | 231 | 461 | 1176 |
| Mean Particle Size of Salt Crystal ($\mu$m) | | 620 | 450 | 550 | 630 | 630 | 640 |
| Liquid Content of Crystal after rinsing (%) | | 1.8 | 3.2 | 2.2 | 1.7 | 1.7 | 1.6 |
| Property of Wet Crystal Cake | | good | good | good | good | good | good |
| Quality of NDCA-TEA Crystal[a] | Hue OD400 | 0.32 | 0.39 | 0.35 | 0.31 | 0.30 | 0.29 |
| | Organic Purity (%) | | | | | | |
| | NDCA | 99.78 | 99.62 | 99.72 | 99.79 | 99.79 | 99.80 |
| | NA | 0.0053 | 0.010 | 0.0078 | 0.0051 | 0.0051 | 0.0050 |
| | MNA | 0.0012 | 0.0014 | 0.0013 | 0.0011 | 0.0011 | 0.0010 |
| | TMA | 0.023 | 0.085 | 0.051 | 0.021 | 0.021 | 0.020 |
| | FNA | 0.0078 | 0.019 | 0.013 | 0.0075 | 0.0074 | 0.0074 |
| | ANA | 0.0066 | 0.0092 | 0.0076 | 0.0065 | 0.0065 | 0.0065 |
| | Br-NDCA | 0.013 | 0.027 | 0.019 | 0.012 | 0.012 | 0.011 |
| | NTCA | 0.13 | 0.17 | 0.15 | 0.13 | 0.13 | 0.13 |
| Quality of Purified Naphthalenedi- | Hue OD400 | 0.20 | 0.24 | 0.22 | 0.19 | 0.19 | 0.18 |
| | Organic Purity (%) | | | | | | |
| carboxylic Acid Obtained through Salt Decomposition | NDCA | 99.97 | 99.81 | 99.91 | 99.98 | 99.98 | 99.99 |
| | NA | 0.0009 | 0.0017 | 0.0013 | 0.0009 | 0.0009 | 0.0008 |
| | MNA | 0.0004 | 0.0005 | 0.0004 | 0.0004 | 0.0004 | 0.0003 |
| | TMA | 0.0008 | 0.0030 | 0.0018 | 0.0007 | 0.0007 | 0.0007 |
| | FNA | 0.0009 | 0.0022 | 0.0015 | 0.0009 | 0.0009 | 0.0009 |
| | ANA | 0.0029 | 0.0040 | 0.0033 | 0.0029 | 0.0029 | 0.0029 |
| | Br-NDCA | 0.0014 | 0.0030 | 0.0021 | 0.0013 | 0.0013 | 0.0012 |
| | NTCA | 0.0094 | 0.012 | 0.011 | 0.0095 | 0.0095 | 0.0095 |

[a]: Quality of naphthalenedicarboxylic acid-containing crystal obtained through vacuum drying of NDCA-TEA crystal

TABLE 2

|  |  | Comparative Example A1 | Comparative Example A2 | Comparative Example A3 | Comparative Example A4 |
|---|---|---|---|---|---|
| Amine Addition Rate (relative to NDCA, mol/min) | | about 15 | 0.49 | 0.81 | 0.0011 |
| Time taken by TEA addition (min) | | about 0.17 | 5 | 3 | 2308 |
| Mean Particle Size of Salt Crystal ($\mu$m) | | 180 | 400 | 360 | 640 |
| Liquid Content of Crystal after rinsing (%) | | 10 | 4.0 | 5.0 | 1.6 |
| Property of Wet Crystal Cake | | bad | problematic | problematic | good |
| Quality of NDCA-TEA Crystal[a] | Hue OD400 | 0.64 | 0.43 | 0.47 | 0.29 |
| | Organic Purity (%) | | | | |
| | NDCA | 99.02 | 99.59 | 99.49 | 99.80 |
| | NA | 0.026 | 0.012 | 0.015 | 0.0050 |
| | MNA | 0.0028 | 0.0015 | 0.0017 | 0.0010 |
| | TMA | 0.48 | 0.11 | 0.16 | 0.020 |
| | FNA | 0.069 | 0.023 | 0.031 | 0.0073 |
| | ANA | 0.022 | 0.010 | 0.012 | 0.0065 |
| | Br-NDCA | 0.085 | 0.033 | 0.042 | 0.011 |
| | NTCA | 0.32 | 0.18 | 0.20 | 0.13 |

[a] Quality of naphthalenedicarboxylic acid-containing crystal obtained through vacuum drying of NDCA-TEA crystal The details of the apparatuses used in Examples B1 to B21 and Comparative Examples B1 to B3 are described below.

Standard separation plate-type centrifugal settler: Alfa Laval's disc-type centrifuge, Model LAPX404.

Decanter-type centrifuge: Mitsubishi Kakoki's mini-vane decanter, Model DS100V.

Horizontal filter leaf-type pressure strainer: IHI's leaf filter, Model CFR 0.5-3-50, filtration area 0.5 m².

Automatic filter paper-exchange pressure filter: Mitsubishi Kakoki's Schneider filter, Model CF-20-S4, filtration area 0.2 m².

Oscillating membrane separator: Techno Alpha's V-SEP, L-mode, filtration area 0.046 m², MF 0.45-$\mu$m membrane used.

Ceramic membrane filter: NGK Insulators' test machine, filtration area 0.35 m², Cefilt MF 0.1-$\mu$m membrane used.

Production Example B1

With reference to the production example in PTL 6, a crude naphthalenedicarboxylic acid was obtained through oxidation of 2,6-dimethylnaphthalene.

0.38 kg of cobalt acetate (4-hydrate), 3.2 kg of manganese acetate (4-hydrate) and 0.743 kg of hydrogen bromide (47% aqueous solution) were mixed and dissolved in 179.7 kg of glacial acetic acid to prepare a catalyst liquid. 74 g of the catalyst liquid was put into a 500-L titanium-made autoclave equipped with a stirrer, a reflux condenser and a starting material feeding pump. The remaining catalyst liquid was mixed with 18 kg of 2,6-dimethylnaphthalene, put into a starting material supply tank, and heated therein to dissolve 2,6-dimethylnaphthalene to prepare a starting material liquid. The reaction system was purged with nitrogen to have an inner pressure of 1.8 MPaG, and with stirring, this was heated up to 200° C. After the temperature and the pressure were stabilized, the starting material liquid and compressed air were fed into the reactor to start oxidation. While the quantity of air flow to be supplied was so controlled that the oxygen concentration in the off-gas from the reactor could be 1.0% by volume, the starting material liquid was continuously supplied into the system, taking 2 hours. After the supply of the starting material liquid, air supply was still continued for 9 minutes. After the reaction, the reactor was cooled down to room temperature, then the reaction product was taken out, and using Nutsche, this was filtered under suction, then washed with water and acetic acid, and dried. As a result, there was obtained a crude naphthalenedicarboxylic acid having an NDCA purity of 98.60% and containing 2600 ppm of FNA, 360 ppm of cobalt and 2500 ppm of manganese.

Production Example B2

With reference to Example 21 in PTL 5, a crystal of NDCA-TEA was obtained through salt-formation and crystallization.

20 kg of the crude naphthalenedicarboxylic acid obtained in Production Example B1, 16 kg of acetone and 12 kg of water (water content of solvent, 42.8%) were put into a 200-liter, SUS316L-made reactor equipped with a reflux condenser, a stirrer and a thermometric duct, then 20 kg of TEA was added thereto and stirred and mixed for 30 minutes for salt formation while kept at 25° C. Next, 64.4 kg of acetone was added thereto, stirred and mixed for 30 minutes to thereby precipitate an NDCA-TEA crystal. At 25° C., the NDCA-TEA crystal-containing slurry was centrifuged with a basket-type centrifuge, and then the crystal on the filter cloth of the basket-type centrifuge was rinsed with 30 kg of acetone. As a result, 41.4 kg of NDCA-TEA crystal was obtained. The NDCA-TEA crystal was dried at 100° C. in vacuum for 3 hours. Thus obtained, the naphthalenedicarboxylic acid-containing crystal had an NDCA purity of 99.88% and contained 170 ppm of FNA, 360 ppm of cobalt and 2500 ppm of manganese, and the NDCA recovery rate was 98.0%. The operation was repeated ten times to give 415 kg of NDCA-TEA.

Example B1

15 kg of the NDCA-TEA crystal obtained in Production Example B2 and 15 kg of water were put into a 50-liter, SUS316L-made reactor equipped with a stirrer and a thermometric duct, and the NDCA-TEA crystal was dissolved. Next, in a nitrogen atmosphere, 373 g (10 equivalents) of TEA was added thereto and stirred at 70° C. for 30 minutes for insolubilization. In a nitrogen atmosphere at 70° C., the resulting solution was fed into a horizontal filter leaf-type pressure strainer and filtered to separate the metal component. In filtration in the horizontal filter leaf-type pressure strainer, used were a mixture of Radiolite #100 and Radiolite #800S (both by Showa Chemical Industry) serving as a filtration aid for precoating and Radiolite #800S as a filtration aid for body feeding. 700 g of the solution was put into a 3-liter, SUS316L-made autoclave equipped with a stirrer, a pressure filter and a degassing port, the purged with nitrogen, heated up to 200° C., and while water was added thereto at a rate of 100 g/hr at the temperature, the same amount as that of the supplied water of the distillate was extracted out through the top of the reactor, and this extraction operation was continued for 2 hours. The total amount of the extracted distillate was about 21 times the amount of NDCA in the solution. Next, at the same temperature, this was filtered under pressure, and the resulting crystal was washed with water, and dried in vacuum at 120° C. for 5 hours to give a purified naphthalenedicarboxylic acid as shown in Table 3.

Example B2

A purified naphthalenedicarboxylic acid as shown in Table 3 was obtained in the same manner as in Example B1 except that 746 g of TEA was added for insolubilization.

Example B3

A purified naphthalenedicarboxylic acid as shown in Table 3 was obtained in the same manner as in Example B2 except that an automatic filter paper-exchange pressure filter was used in filtration.

Example B4

A purified naphthalenedicarboxylic acid as shown in Table 3 was obtained in the same manner as in Example B2 except that an oscillating membrane separator was used in filtration. In this case, a filtration aid was not used.

Example B5

15 kg of the NDCA-TEA crystal obtained in Production Example B2 and 15 kg of water were put into a 50-liter, SUS316L-made reactor, and the NDCA-TEA crystal was dissolved. At 70° C., the solution was fed into a horizontal filter leaf-type pressure strainer and filtered to separate the metal component, and the resulting filtrate was received by a 50-liter SUS316L-made reactor equipped with a stirrer and a thermometric duct. In filtration in the horizontal filter leaf-type pressure strainer, used were a mixture of Radiolite #100 and Radiolite #800S serving as a filtration aid for precoating and Radiolite #800S as a filtration aid for body feeding. Next in a nitrogen atmosphere, 746 g of TEA was added thereto and stirred for 30 minutes at 70° C. for insolubilization. In a nitrogen atmosphere at 70° C., the resulting solution was fed into a ceramic membrane filter and filtered to separate the metal component. During the filtration through the ceramic membrane filter, the system was back-washed with the filtrate at intervals of 10 minutes. Subsequently, the system was processed in the same manner as in Example B1 to give a purified naphthalenedicarboxylic acid as shown in Table 3.

Example B6

A purified naphthalenedicarboxylic acid as shown in Table 3 was obtained in the same manner as in Example B5 except that an automatic filter paper-exchange pressure filter was used in the first-stage filtration.

Example B7

A purified naphthalenedicarboxylic acid as shown in Table 3 was obtained in the same manner as in Example B5 except that an oscillating membrane separator was used in the first-stage filtration. A filtration aid was not used during the filtration in the oscillating membrane separator.

Example B8

A purified naphthalenedicarboxylic acid as shown in Table 3 was obtained in the same manner as in Example B7 except that an oscillating membrane separator was used in the second-stage filtration.

Example B9

15 kg of the NDCA-TEA crystal obtained in Production Example B2 and 15 kg of water were put into a 50-liter, SUS316L-made reactor, and the NDCA-TEA crystal was dissolved. At 70° C., the solution was fed into a horizontal filter leaf-type pressure strainer and filtered, and the resulting filtrate was received by a 50-liter SUS316L-made reactor equipped with a stirrer and a thermometric duct. In filtration in the horizontal filter leaf-type pressure strainer, used were a mixture of Radiolite #100 and Radiolite #800S serving as a filtration aid for precoating and Radiolite #800S as a filtration aid for body feeding. Next in a nitrogen atmosphere, 746 g of TEA was added thereto and stirred for 30 minutes at 70° C. for insolubilization. In a nitrogen atmosphere at 70° C., the thus-insolubilized liquid was fed into a standard separation plate-type centrifugal settler at a rate of 2 L/min to separate the metal component. Subsequently, in the same manner as in Example B1, a purified naphthalenedicarboxylic acid A as shown in Table 3 was obtained.

Example B10

A purified naphthalenedicarboxylic acid as shown in Table 3 was obtained in the same manner as in Example B9 except that an oscillating membrane separator was used in the first-stage filtration. A filtration aid was not used during the filtration in the oscillating membrane separator.

Example B11

15 kg of the NDCA-TEA crystal obtained in Production Example 2 and 15 kg of water were put into a 50-liter, SUS316L-made reactor equipped with a stirrer and a thermometric duct, and the NDCA-TEA crystal was dissolved. Next, in a nitrogen atmosphere, 746 g of TEA was added thereto, and stirred at 70° C. for 30 minutes for insolubilization. In a nitrogen atmosphere at 70° C., the thus-insolubilized liquid was fed into a standard separation plate-type centrifugal settler at a rate of 1 L/min to separate the metal component. Subsequently, in the same manner as in Example 1, a purified naphthalenedicarboxylic acid as shown in Table 3 was obtained.

Example B12

15 kg of the NDCA-TEA crystal obtained in Production Example B2 and 15 kg of water were put into a 50-liter, SUS316L-made reactor equipped with a stirrer and a thermometric duct, and the NDCA-TEA crystal was dissolved. Next, in a nitrogen atmosphere, 746 g of TEA was added thereto, and stirred at 70° C. for 30 minutes for insolubilization. In a nitrogen atmosphere at 70° C., the thus-insolubilized liquid was fed into a decanter-type centrifuge at a rate of 1 L/min to separate the metal component, and the solution was received by a 50-liter SUS316L-made reactor. In a nitrogen atmosphere at 70° C., the solution was fed into a standard separation plate-type centrifugal settler at a rate of 2 L/min, and the metal component was separated. Subsequently, in the same manner as in Example B1, a purified naphthalenedicarboxylic acid as shown in Table 3 was obtained.

Example B13

15 kg of the NDCA-TEA crystal obtained in Production Example B2 and 15 kg of water were put into a 50-liter, SUS316L-made reactor, and the NDCA-TEA crystal was dissolved. At 70° C., the solution was fed into a decanter-type centrifuge at a rate of 1 L/min to separate the metal component, and the solution was received by a 50-liter, SUS316L-made reactor equipped with a stirrer and a thermometric duct. Next, in a nitrogen atmosphere, 746 g of TEA was added thereto, and stirred at 70° C. for 30 minutes for insolubilization. In a nitrogen atmosphere at 70° C., the thus-insolubilized liquid was fed into a standard separation plate-type centrifugal settler at a rate of 2 L/min to separate the metal component. Subsequently, in the same manner as in Example B1, a purified naphthalenedicarboxylic acid as shown in Table 3 was obtained.

Example B14

In the same manner as in Example B11, the metal was removed in a standard separation plate-type centrifugal settler, except that the liquid was fed at a rate of 2 L/min. In a nitrogen atmosphere at 70° C., the resulting solution was fed into a horizontal filter leaf-type pressure strainer, and filtered. In filtration in the horizontal filter leaf-type pressure strainer, used were a mixture of Radiolite #100 and Radiolite #800S serving as a filtration aid for precoating and Radiolite #800S as a filtration aid for body feeding. In the same manner as in Example B1 after the filtration in the horizontal filter leaf-type pressure strainer, a purified naphthalenedicarboxylic acid as shown in Table 3 was obtained.

Example B15

15 kg of the NDCA-TEA crystal obtained in Production Example B2 and 15 kg of water were put into a 50-liter, SUS316L-made reactor, and the NDCA-TEA crystal was dissolved. At 70° C., the solution was fed into a standard separation plate-type centrifugal settler at a rate of 2 L/min to separate the metal component, and the solution was received by a 50-liter, SUS316L-made reactor equipped with a stirrer and a thermometric duct. Next, in a nitrogen atmosphere, 746 g of TEA was added thereto, and stirred at 70° C. for 30 minutes for insolubilization. After the insolubilization, using a horizontal filter-leaf type pressure strainer and in the same manner as in Example B14, a purified naphthalenedicarboxylic acid as shown in Table 3 was obtained.

Example B16

A purified naphthalenedicarboxylic acid as shown in Table 3 was obtained in the same manner as in Example B14 except that an automatic filter paper-exchange pressure filter was used in the second-stage filtration.

Example B17

A purified naphthalenedicarboxylic acid as shown in Table 3 was obtained in the same manner as in Example B15 except that an automatic filter paper-exchange pressure filter was used in the second-stage filtration.

Example B18

A purified naphthalenedicarboxylic acid as shown in Table 3 was obtained in the same manner as in Example B14 except that an oscillating membrane separator was used in the second-stage filtration. A filtration aid was not used during the filtration using the oscillating membrane separator.

Example B19

A purified naphthalenedicarboxylic acid as shown in Table 3 was obtained in the same manner as in Example B15 except that an oscillating membrane separator was used in the second-stage filtration. A filtration aid was not used during the filtration using the oscillating membrane separator.

Example B20

A purified naphthalenedicarboxylic acid as shown in Table 3 was obtained in the same manner as in Example B14 except that a ceramic membrane filter was used in the second-stage filtration. During the filtration with the ceramic membrane filter, the system was back-washed with the filtrate at intervals of 10 minutes. A filtration aid was not used during the filtration with the ceramic membrane filter.

Example B21

A purified naphthalenedicarboxylic acid as shown in Table 3 was obtained in the same manner as in Example B15 except that a ceramic membrane filter was used in the second-stage filtration. During the filtration with the ceramic membrane filter, the system was back-washed with the filtrate at intervals of 10 minutes. A filtration aid was not used during the filtration with the ceramic membrane filter.

Comparative Example B1

Example 17 in PTL 5 was referred to for the operation here. One kg of the NDCA-TEA crystal obtained in Production Example B2 and 1 kg of water were put into a 3-liter, glass-made reactor, and the NDCA-TEA crystal was dissolved. The solution was precision-filtered through a 1-μm filter to separate the foreign substance and the insoluble metal component. Subsequently, this was processed for salt decomposition in the same manner as in Example B1 to give a purified naphthalenedicarboxylic acid as shown in Table 3. As processed for salt formation and crystallization, the thus-obtained purified naphthalenedicarboxylic acid had no problem in point of the FNA fraction; however, as not processed for insolubilization, the product had a high residual metal content.

Comparative Example B2

Example 1 in PTL 6 was referred to for the operation here. 200 g of the crude naphthalenedicarboxylic acid obtained in Production Example B1, 1070 g of water and 205.9 g (1.1 equivalents relative to NDCA) of TEA were put into a 2-liter glass-made, four-neck flask equipped with a reflux condenser, a stirrer and a thermometric duct, and stirred for 30 minutes. The metal component that had not dissolved but precipitated was removed by filtration through a sintered metal filter having a pore size of 10 μm, and further filtered through a filter having a pore size of 5 μm. Subsequently, this was processed for salt decomposition in the same manner as in Example B1 to give a purified naphthalenedicarboxylic acid as shown in Table 3. The FNA component content and the metal component content in the thus-obtained, purified naphthalenedicarboxylic acid were both high.

Comparative Example B3

Example 3 in PTL 6 was referred to for the operation here. 200 g of the crude naphthalenedicarboxylic acid obtained in Production Example B1, 1070 g of water and 205.9 g (1.1 equivalents relative to NDCA) of TEA were put into a 2-liter glass-made, four-neck flask equipped with a reflux condenser, a stirrer and a thermometric duct, and stirred for 30 minutes. The metal component that had not dissolved but precipitated was removed by filtration through a sintered metal filter having a pore size of 10 μm, and further filtered through a nitrocellulose-made membrane filter having a pore size of 1 μm. Further, this was led to pass a glass column filled with active carbon. Subsequently, this was processed for salt decomposition in the same manner as in Example B1 to give a purified naphthalenedicarboxylic acid as shown in Table 3. The thus-obtained purified naphthalenedicarboxylic acid has no problem except that its FNA level was 200 ppm and was slightly high. However, the operation was extremely complicated.

TABLE 3

| | Sequence of Metal Component Separation Process | Separator Used | | TEA Addition Amount for Insolubilization (equivalent) |
|---|---|---|---|---|
| | | First Stage | Second Stage | |
| Example B1 | Insolubilization → Filtration | horizontal filter leaf-type pressure strainer | — | 10 |
| Example B2 | Insolubilization → Filtration | horizontal filter leaf-type pressure strainer | — | 20 |
| Example B3 | Insolubilization → Filtration | automatic filter paper-exchange pressure filter | — | 20 |
| Example B4 | Insolubilization → Filtration | oscillating membrane separator | — | 20 |

TABLE 3-continued

Table 3

| | | | | |
|---|---|---|---|---|
| Example B5 | Filtration → Insolubilization → Filtration | horizontal filter leaf-type pressure strainer | ceramic membrane filter | 20 |
| Example B6 | Filtration → Insolubilization → Filtration | automatic filter paper-exchange pressure filter | ceramic membrane filter | 20 |
| Example B7 | Filtration → Insolubilization → Filtration | oscillating membrane separator | ceramic membrane filter | 20 |
| Example B8 | Filtration → Insolubilization → Filtration | oscillating membrane separator | oscillating membrane separator | 20 |
| Example B9 | Filtration → Insolubilization → Centrifugal Sedimentation | horizontal filter leaf-type pressure strainer | standard separation plate-type centrifugal settler | 20 |
| Example B10 | Filtration → Insolubilization → Centrifugal Sedimentation | oscillating membrane separator | standard separation plate-type centrifugal settler | 20 |
| Example B11 | Insolubilization → Centrifugal Sedimentation | standard separation plate-type centrifugal settler | — | 20 |
| Example B12 | Insolubilization → Centrifugal Sedimentation → Centrifugal Sedimentation | decanter-type centrifuge | standard separation plate-type centrifugal settler | 20 |
| Example B13 | Centrifugal Sedimentation → Insolubilization → Centrifugal Sedimentation | decanter-type centrifuge | standard separation plate-type centrifugal settler | 20 |
| Example B14 | Insolubilization → Centrifugal Sedimentation → Filtration | standard separation plate-type centrifugal settler | horizontal filter leaf-type pressure strainer | 20 |
| Example B15 | Centrifugal Sedimentation → Insolubilization → Filtration | standard separation plate-type centrifugal settler | horizontal filter leaf-type pressure strainer | 20 |
| Example B16 | Insolubilization → Centrifugal Sedimentation → Filtration | standard separation plate-type centrifugal settler | automatic filter paper-exchange pressure filter | 20 |
| Example B17 | Centrifugal Sedimentation → Insolubilization → Filtration | standard separation plate-type centrifugal settler | automatic filter paper-exchange pressure filter | 20 |
| Example B18 | Insolubilization → Centrifugal Sedimentation → Filtration | standard separation plate-type centrifugal settler | oscillating membrane separator | 20 |
| Example B19 | Centrifugal Sedimentation → Insolubilization → Filtration | standard separation plate-type centrifugal settler | oscillating membrane separator | 20 |
| Example B20 | Insolubilization → Centrifugal Sedimentation → Filtration | standard separation plate-type centrifugal settler | ceramic membrane filter | 20 |
| Example B21 | Centrifugal Sedimentation → Insolubilization → Filtration | standard separation plate-type centrifugal settler | ceramic membrane filter | 20 |
| Comparative Example B1 | Not insolubilized → Filtration | 1 μm filter | — | — |
| Comparative Example B2 | Dissolution of Crude NDCA and TEA in Water → Filtration → Filtration | 10 μm metal sintered filter | 5 μm filter | — |
| Comparative Example B3 | Dissolution of Crude NDCA and TEA in Water → Filtration → Filtration → Treatment with Active Carbon | 10 μm metal sintered filter | 1 μm nitrocellulose membrane filter | — |

| | Product Property | | | | |
|---|---|---|---|---|---|
| | NDCA (%) | FNA (ppm) | Co (ppm) | Mn (ppm) | OD400 |
| Example B1 | 99.98 | 30 | 1.0 | 1.4 | 0.40 |
| Example B2 | 99.98 | 30 | 0.7 | 0.8 | 0.40 |
| Example B3 | 99.98 | 25 | 0.8 | 0.9 | 0.40 |
| Example B4 | 99.99 | 25 | 0.6 | 0.6 | 0.39 |
| Example B5 | 99.99 | 30 | <0.5 | <0.5 | 0.38 |
| Example B6 | 99.99 | 30 | <0.5 | <0.5 | 0.37 |
| Example B7 | 99.99 | 30 | <0.5 | <0.5 | 0.36 |
| Example B8 | 99.99 | 25 | <0.5 | <0.5 | 0.36 |
| Example B9 | 99.99 | 30 | <0.5 | <0.5 | 0.40 |
| Example B10 | 99.99 | 25 | <0.5 | <0.5 | 0.40 |

TABLE 3-continued

Table 3

| | | | | | |
|---|---|---|---|---|---|
| Example B11 | 99.97 | 30 | 1.6 | 1.9 | 0.42 |
| Example B12 | 99.96 | 25 | 1.1 | 1.3 | 0.41 |
| Example B13 | 99.98 | 25 | 0.7 | 1.0 | 0.40 |
| Example B14 | 99.99 | 20 | <0.5 | <0.5 | 0.38 |
| Example B15 | 99.99 | 25 | <0.5 | <0.5 | 0.38 |
| Example B16 | 99.99 | 30 | <0.5 | <0.5 | 0.39 |
| Example B17 | 99.99 | 25 | <0.5 | <0.5 | 0.38 |
| Example B18 | 99.99 | 20 | <0.5 | <0.5 | 0.36 |
| Example B19 | 99.99 | 25 | <0.5 | <0.5 | 0.37 |
| Example B20 | 99.99 | 30 | <0.5 | <0.5 | 0.38 |
| Example B21 | 99.99 | 25 | <0.5 | <0.5 | 0.38 |
| Comparative Example B1 | 99.96 | 70 | 6.0 | 12.0 | 0.44 |
| Comparative Example B2 | 99.75 | 2050 | 11 | 70 | 0.55 |
| Comparative Example B3 | 99.80 | 200 | <0.5 | <0.5 | 0.45 |

In Examples B1 to B21 and Comparative Example B1, Sequence of Metal Component Separation Process is described with the dissolution of NDCA-TEA in water omitted.

Industrial Applicability

According to the production method for a purified naphthalenedicarboxylic acid in the first aspect of the present invention, the crystal of the naphthalenedicarboxylic acid amine salt that is a production intermediate for the purified naphthalenedicarboxylic acid has a high purity and has a large particle size. Since the particle size of the amine salt crystal is large:

(1) solid-liquid separation is easy,
(2) there occurs no clogging during discharge and transfer of the crystal cake, and it is easy to discharge and transfer the cake,
(3) the liquid content of the amine salt crystal (the content of mother liquid and rinsing liquid in the salt crystal) is low, and the process cost can be reduced.

Accordingly, a purified naphthalenedicarboxylic acid can be produced industrially advantageously. The industrial significance of the present invention is great for naphthalenedicarboxylic acid purification.

According to the production method for a purified naphthalenedicarboxylic acid in the second aspect of the present invention, an amine is added to an aqueous solution of a naphthalenedicarboxylic acid amine salt or to a liquid obtained through solid-liquid separation of an aqueous solution of a naphthalenedicarboxylic acid amine salt to thereby promote the precipitation of the metal component. Consequently, a purified naphthalenedicarboxylic acid can be produced with ease according to an industrial and simplified method at a low production cost. The method of the present invention is an industrially excellent method, and therefore the industrial significance of the present invention is extremely great.

The invention claimed is:

1. A method for producing a purified naphthalenedicarboxylic acid, comprising:
   (A1) a step of mixing a naphthalenedicarboxylic acid-containing material and an amine in a mixed liquid of water and an organic solvent to give a crystal of a naphthalenedicarboxylic acid amine salt; and
   (A2) a step of obtaining a purified naphthalenedicarboxylic acid from the crystal of the naphthalenedicarboxylic acid amine salt obtained in the step (A1), wherein:
   the step (A1) comprises:
      (A11) a step of adding a naphthalenedicarboxylic acid-containing material to a mixed liquid of water and an organic solvent to prepare a slurry in which the naphthalenedicarboxylic acid has dispersed therein;
      (A12) a step of adding an amine to the slurry prepared in the step (A11) to form a naphthalenedicarboxylic acid amine salt, thereby preparing a slurry in which a crystal of the naphthalenedicarboxylic acid amine salt has dispersed; and
      (A13) a step of processing the slurry prepared in the step (A12) for solid-liquid separation to separate the crystal of the naphthalenedicarboxylic acid amine salt, and
   the amine addition rate in the step (A12) is from 0.002 to 0.4 mol/min relative to one mol of the naphthalenedicarboxylic acid.

2. The method for producing a purified naphthalenedicarboxylic acid according to claim 1, wherein the naphthalenedicarboxylic acid-containing material in the step (A1) is one prepared by oxidizing a naphthalene having two substituents with a molecular oxygen in the presence of an oxidation catalyst.

3. The method for producing a purified naphthalenedicarboxylic acid according to claim 1, wherein the organic solvent in the step (A1) is a ketone.

4. The method for producing a purified naphthalenedicarboxylic acid according to claims 1, wherein the amine added in the step (A12) is a tertiary aliphatic amine.

5. The method for producing a purified naphthalenedicarboxylic acid according to claims 1, wherein the step (A2) comprises:
   (A21) a step of dissolving the crystal of the naphthalenedicarboxylic acid amine salt obtained in the step (A1), in water to thereby prepare an aqueous solution of the naphthalenedicarboxylic acid amine salt; and
   (A22) a step of obtaining a purified naphthalenedicarboxylic acid from the aqueous solution of the naphthalenedicarboxylic acid amine salt prepared in the step (A21).

6. A method for producing a purified naphthalenedicarboxylic acid, comprising:
   (B1) a step of mixing a naphthalenedicarboxylic acid-containing material and an amine in a mixed liquid of water and an organic solvent to give a crystal of a naphthalenedicarboxylic acid amine salt; and
   (B2) a step of obtaining a purified naphthalenedicarboxylic acid from the crystal of the naphthalenedicarboxylic acid amine salt obtained in the step (B1), wherein:
   the step (B2) comprises:

(B21) a step of dissolving the crystal of the naphthalenedicarboxylic acid amine salt obtained in the step (B1) in water to prepare an aqueous solution of the naphthalenedicarboxylic acid amine salt;

(B22) a step of removing a metal component from the aqueous solution of the naphthalenedicarboxylic acid amine salt prepared in the step (B21); and (B23) a step of obtaining a purified naphthalenedicarboxylic acid from the aqueous solution of the naphthalenedicarboxylic acid amine salt from which the metal component has been removed in the step (B22), and in the step (B22), the metal component is removed from the aqueous solution of the naphthalenedicarboxylic acid amine salt through:

(a) treatment of adding an amine to the aqueous solution of the naphthalenedicarboxylic acid amine salt prepared in the step (B21) to thereby insolubilize and precipitate the metal component contained in the aqueous solution, followed by removing the precipitated metal component though solid-liquid separation; or (b) treatment of adding an amine to a liquid obtained through solid-liquid separation of the aqueous solution of the naphthalenedicarboxylic acid amine salt prepared in the step (B21) to thereby insolubilize and precipitate the metal component contained in the liquid obtained through the solid-liquid separation, followed by removing the precipitated metal component though solid-liquid separation.

7. The method for producing a purified naphthalenedicarboxylic acid according to claim 6, wherein the amount of the amine added in the step (B22) is from 1 equivalent to 100 equivalents relative to the total amount of metal dissolved in the aqueous solution of the naphthalenedicarboxylic acid amine salt.

8. The method for producing a purified naphthalenedicarboxylic acid according to claim 6, wherein the solid-liquid separation in the treatment (a) in the step (B22) is according to a method selected from the group consisting of one-time filtration, two-time filtration, filtration followed by centrifugal sedimentation, one-time centrifugal sedimentation, two-time centrifugal sedimentation, and centrifugal sedimentation followed by filtration.

9. The method for producing a purified naphthalenedicarboxylic acid according to claim 6, wherein the solid-liquid separation before the amine addition in the treatment (b) in the step (B22) is through one-time filtration or one-time centrifugal sedimentation, and the solid-liquid separation after the amine addition in the treatment (b) is through one-time filtration or one-time centrifugal sedimentation.

10. The method for producing a purified naphthalenedicarboxylic acid according to claim 8, wherein as the filtration device in the step (B22), used is a horizontal filter leaf-type pressure strainer, an automatic filter paper-exchange pressure filter, an oscillating membrane separator or a ceramic membrane filter, and as the centrifugal settling device therein, used is a decanter-type centrifuge or a standard separation plate-type centrifugal settler.

11. The method for producing a purified naphthalenedicarboxylic acid according to claims 6, wherein the amine in the step (B22) is a tertiary aliphatic amine.

12. The method for producing a purified naphthalenedicarboxylic acid according to claims 6, wherein the naphthalenedicarboxylic acid-containing material in the step (B1) is one prepared by oxidizing a naphthalene having two substituents with a molecular oxygen in the presence of an oxidation catalyst.

13. The method for producing a purified naphthalenedicarboxylic acid according to claims 6, wherein the organic solvent in the step (B1) is a ketone.

14. The method for producing a purified naphthalenedicarboxylic acid according to claims 6, wherein the amine in the step (B1) is a tertiary aliphatic amine.

15. The method for producing a purified naphthalenedicarboxylic acid according to claims 6, wherein in the step (B23), the aqueous solution of the naphthalenedicarboxylic acid amine salt from which the metal component has been removed in the step (B22) is heated in the presence of water to decompose the amine salt and to evaporate and remove water and the amine, thereby precipitating a purified naphthalenedicarboxylic acid in the aqueous solution so as to obtain the purified naphthalenedicarboxylic acid.

\* \* \* \* \*